(12) United States Patent  
Horvath et al.

(10) Patent No.: US 8,974,511 B2
(45) Date of Patent: Mar. 10, 2015

(54) METHODS FOR TREATING CLOSED ANGLE GLAUCOMA

(75) Inventors: Christopher Horvath, Desert Hot Springs, CA (US); Laszlo O. Romoda, San Clemente, CA (US)

(73) Assignee: AqueSys, Inc., Aliso Viejo, CA (US)

( * ) Notice: Subject to any disclaimer, the term of this patent is extended or adjusted under 35 U.S.C. 154(b) by 554 days.

(21) Appl. No.: 12/946,565

(22) Filed: Nov. 15, 2010

(65) Prior Publication Data

US 2012/0123437 A1    May 17, 2012

(51) Int. Cl.
*A61F 2/06* (2013.01)
*A61F 9/007* (2006.01)

(52) U.S. Cl.
CPC ................ *A61F 9/00781* (2013.01)
USPC .................. 623/1.11; 606/107; 604/8; 604/9

(58) Field of Classification Search
USPC .......... 623/1.11, 1.41, 8, 9, 10; 606/107, 108, 606/166; 604/8, 9, 521, 408, 409
See application file for complete search history.

(56) References Cited

U.S. PATENT DOCUMENTS

| | | |
|---|---|---|
| 3,788,327 A | 1/1974 | Donowitz et al. |
| 3,960,150 A | 6/1976 | Hussain et al. |
| 4,090,530 A | 5/1978 | Lange |
| 4,722,724 A | 2/1988 | Schocket |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,863,457 A | 9/1989 | Lee |
| 4,902,292 A | 2/1990 | Joseph |
| 4,911,161 A | 3/1990 | Schechter |
| 4,915,684 A | 4/1990 | Mackeen et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |

(Continued)

FOREIGN PATENT DOCUMENTS

| | | |
|---|---|---|
| GB | 2 296 663 A | 7/1996 |
| WO | WO 94/13234 A1 | 6/1994 |

(Continued)

OTHER PUBLICATIONS

International Search Report in PCT application No. PCT/US2007/072547, mailed May 23, 2008, 7 pages.

(Continued)

*Primary Examiner* — Gary Jackson
*Assistant Examiner* — Katrina Stransky
(74) *Attorney, Agent, or Firm* — James W. Hill; McDermott Will & Emery LLP

(57) ABSTRACT

The present invention generally relates to methods for treating closed angle glaucoma. In certain embodiments, methods of the invention involve inserting into an eye a deployment device configured to hold an intraocular shunt, using the device to re-open an at least partially closed anterior chamber angle of an eye, and deploying the shunt from the device.

24 Claims, 24 Drawing Sheets

(56) References Cited

U.S. PATENT DOCUMENTS

| | | | |
|---|---|---|---|
| 5,092,837 A | 3/1992 | Ritch et al. | |
| 5,098,443 A | 3/1992 | Parel et al. | |
| 5,178,604 A | 1/1993 | Baerveldt et al. | |
| 5,180,362 A * | 1/1993 | Worst | 604/8 |
| 5,275,622 A | 1/1994 | Lazarus et al. | |
| 5,290,295 A | 3/1994 | Querals et al. | |
| 5,300,020 A | 4/1994 | L'Esperance, Jr. | |
| 5,333,619 A | 8/1994 | Burgio | |
| 5,338,291 A | 8/1994 | Speckman et al. | |
| 5,342,370 A | 8/1994 | Simon et al. | |
| 5,360,339 A | 11/1994 | Rosenberg | |
| 5,370,607 A | 12/1994 | Memmen | |
| 5,476,445 A | 12/1995 | Baerveldt et al. | |
| 5,516,522 A | 5/1996 | Peyman et al. | |
| 5,520,631 A | 5/1996 | Nordquist et al. | |
| 5,558,629 A | 9/1996 | Baerveldt et al. | |
| 5,558,630 A | 9/1996 | Fisher | |
| 5,601,094 A | 2/1997 | Reiss | |
| 5,665,093 A | 9/1997 | Atkins et al. | |
| 5,665,114 A | 9/1997 | Weadock et al. | |
| 5,670,161 A | 9/1997 | Healy et al. | |
| 5,688,562 A | 11/1997 | Hsiung | |
| 5,695,474 A | 12/1997 | Daugherty | |
| 5,702,414 A | 12/1997 | Richter et al. | |
| 5,704,907 A | 1/1998 | Nordquist et al. | |
| 5,722,948 A | 3/1998 | Gross | |
| 5,743,868 A | 4/1998 | Brown et al. | |
| 5,763,491 A | 6/1998 | Brandt et al. | |
| 5,868,697 A | 2/1999 | Richter et al. | |
| 5,893,837 A * | 4/1999 | Eagles et al. | 604/9 |
| 5,908,449 A | 6/1999 | Bruchman et al. | |
| 5,932,299 A | 8/1999 | Katoot | |
| 5,968,058 A | 10/1999 | Richter et al. | |
| 6,007,511 A | 12/1999 | Prywes | |
| 6,007,578 A | 12/1999 | Schachar | |
| 6,050,970 A | 4/2000 | Baerveldt | |
| 6,086,543 A | 7/2000 | Anderson et al. | |
| 6,102,045 A | 8/2000 | Nordquist et al. | |
| 6,165,210 A | 12/2000 | Lau et al. | |
| 6,203,513 B1 | 3/2001 | Yaron et al. | |
| 6,228,873 B1 | 5/2001 | Brandt et al. | |
| 6,261,256 B1 | 7/2001 | Ahmed | |
| 6,264,665 B1 | 7/2001 | Yu et al. | |
| 6,280,468 B1 | 8/2001 | Schachar | |
| 6,450,937 B1 | 9/2002 | Mercereau et al. | |
| 6,450,984 B1 | 9/2002 | Lynch et al. | |
| 6,464,724 B1 | 10/2002 | Lynch et al. | |
| 6,468,283 B1 | 10/2002 | Richter et al. | |
| 6,471,666 B1 | 10/2002 | Odrich | |
| 6,510,600 B2 | 1/2003 | Yaron et al. | |
| 6,524,275 B1 | 2/2003 | Lynch et al. | |
| 6,533,768 B1 | 3/2003 | Hill | |
| 6,544,249 B1 | 4/2003 | Yu et al. | |
| 6,558,342 B1 | 5/2003 | Yaron et al. | |
| 6,595,945 B2 | 7/2003 | Brown | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,699,210 B2 | 3/2004 | Williams et al. | |
| 6,726,664 B2 | 4/2004 | Yaron et al. | |
| D490,152 S | 5/2004 | Myall et al. | |
| 6,736,791 B1 | 5/2004 | Tu et al. | |
| 6,780,164 B2 | 8/2004 | Bergheim et al. | |
| 6,783,544 B2 | 8/2004 | Lynch et al. | |
| 6,827,699 B2 | 12/2004 | Lynch et al. | |
| 6,827,700 B2 | 12/2004 | Lynch et al. | |
| 6,881,198 B2 | 4/2005 | Brown | |
| 6,939,298 B2 | 9/2005 | Brown et al. | |
| 6,955,656 B2 | 10/2005 | Bergheim et al. | |
| 6,981,958 B1 | 1/2006 | Gharib et al. | |
| 7,008,396 B1 | 3/2006 | Straub | |
| 7,037,335 B2 | 5/2006 | Freeman et al. | |
| 7,041,077 B2 | 5/2006 | Shields | |
| 7,094,225 B2 | 8/2006 | Tu et al. | |
| 7,118,547 B2 | 10/2006 | Dahan | |
| 7,135,009 B2 | 11/2006 | Tu et al. | |
| 7,163,543 B2 | 1/2007 | Smedley et al. | |
| 7,186,232 B1 | 3/2007 | Smedley et al. | |
| 7,207,980 B2 * | 4/2007 | Christian et al. | 604/524 |
| 7,220,238 B2 | 5/2007 | Lynch et al. | |
| 7,291,125 B2 | 11/2007 | Coroneo | |
| 7,331,984 B2 | 2/2008 | Tu et al. | |
| 7,431,710 B2 | 10/2008 | Tu et al. | |
| 7,458,953 B2 | 12/2008 | Peyman | |
| 7,488,303 B1 | 2/2009 | Haffner et al. | |
| 7,563,241 B2 | 7/2009 | Tu et al. | |
| 7,625,384 B2 | 12/2009 | Eriksson et al. | |
| 7,708,711 B2 | 5/2010 | Tu et al. | |
| 7,867,186 B2 | 1/2011 | Haffner et al. | |
| 7,879,001 B2 | 2/2011 | Haffner et al. | |
| 8,109,896 B2 | 2/2012 | Nissan et al. | |
| 8,267,882 B2 | 9/2012 | Euteneuer et al. | |
| 8,277,437 B2 | 10/2012 | Saal et al. | |
| 8,308,701 B2 * | 11/2012 | Horvath et al. | 604/294 |
| 8,337,509 B2 | 12/2012 | Schieber et al. | |
| 8,425,449 B2 | 4/2013 | Wardle et al. | |
| 8,444,589 B2 | 5/2013 | Silvestrini | |
| 8,486,000 B2 | 7/2013 | Coroneo | |
| 8,529,492 B2 | 9/2013 | Clauson et al. | |
| 8,535,333 B2 | 9/2013 | de Juan, Jr. et al. | |
| 8,545,430 B2 | 10/2013 | Silvestrini | |
| 2002/0099434 A1 | 7/2002 | Buscemi et al. | |
| 2002/0133168 A1 | 9/2002 | Smedley et al. | |
| 2002/0177856 A1 | 11/2002 | Richter et al. | |
| 2002/0188308 A1 | 12/2002 | Tu et al. | |
| 2003/0015203 A1 | 1/2003 | Makower et al. | |
| 2003/0050574 A1 | 3/2003 | Krueger | |
| 2003/0060752 A1 * | 3/2003 | Bergheim et al. | 604/27 |
| 2003/0079329 A1 | 5/2003 | Yaron et al. | |
| 2003/0093084 A1 | 5/2003 | Nissan et al. | |
| 2003/0187383 A1 | 10/2003 | Weber et al. | |
| 2003/0229303 A1 | 12/2003 | Haffner et al. | |
| 2003/0236483 A1 | 12/2003 | Ren | |
| 2003/0236484 A1 | 12/2003 | Lynch et al. | |
| 2004/0024345 A1 | 2/2004 | Gharib et al. | |
| 2004/0050392 A1 | 3/2004 | Tu et al. | |
| 2004/0077987 A1 | 4/2004 | Rapacki et al. | |
| 2004/0088048 A1 | 5/2004 | Richter et al. | |
| 2004/0147870 A1 | 7/2004 | Burns et al. | |
| 2004/0216749 A1 | 11/2004 | Tu | |
| 2004/0254521 A1 | 12/2004 | Simon | |
| 2004/0260227 A1 | 12/2004 | Lisk et al. | |
| 2005/0049578 A1 | 3/2005 | Tu et al. | |
| 2005/0125003 A1 | 6/2005 | Pinchuk et al. | |
| 2005/0143363 A1 | 6/2005 | de Juan et al. | |
| 2005/0246023 A1 | 11/2005 | Yeung | |
| 2005/0266047 A1 | 12/2005 | Tu et al. | |
| 2005/0267398 A1 | 12/2005 | Protopsaltis et al. | |
| 2005/0271704 A1 | 12/2005 | Tu et al. | |
| 2005/0277864 A1 | 12/2005 | Haffner et al. | |
| 2005/0288619 A1 | 12/2005 | Gharib et al. | |
| 2006/0052721 A1 | 3/2006 | Dunker et al. | |
| 2006/0064112 A1 | 3/2006 | Perez | |
| 2006/0106370 A1 | 5/2006 | Baerveldt et al. | |
| 2006/0116625 A1 | 6/2006 | Renati et al. | |
| 2006/0149194 A1 | 7/2006 | Conston et al. | |
| 2006/0155238 A1 | 7/2006 | Shields | |
| 2006/0173397 A1 | 8/2006 | Tu et al. | |
| 2006/0173446 A1 | 8/2006 | Dacquay et al. | |
| 2006/0200113 A1 | 9/2006 | Haffner et al. | |
| 2007/0118065 A1 | 5/2007 | Pinchuk et al. | |
| 2007/0118066 A1 | 5/2007 | Pinchuk et al. | |
| 2007/0123812 A1 | 5/2007 | Pinchuk et al. | |
| 2007/0141116 A1 | 6/2007 | Pinchuk et al. | |
| 2007/0172903 A1 | 7/2007 | Toner et al. | |
| 2007/0191863 A1 | 8/2007 | De Juan et al. | |
| 2007/0276315 A1 | 11/2007 | Haffner et al. | |
| 2007/0293872 A1 | 12/2007 | Peyman | |
| 2008/0108933 A1 | 5/2008 | Yu et al. | |
| 2008/0147001 A1 | 6/2008 | Al-Marashi et al. | |
| 2008/0228127 A1 * | 9/2008 | Burns et al. | 604/9 |
| 2008/0281277 A1 | 11/2008 | Thyzel | |
| 2008/0312661 A1 | 12/2008 | Downer et al. | |
| 2009/0036818 A1 | 2/2009 | Grahn et al. | |

(56) References Cited

U.S. PATENT DOCUMENTS

| | | |
|---|---|---|
| 2009/0043321 A1 | 2/2009 | Conston et al. |
| 2009/0082863 A1 | 3/2009 | Schieber et al. |
| 2009/0124973 A1 | 5/2009 | D'Agostino et al. |
| 2009/0132040 A1 | 5/2009 | Frion et al. |
| 2009/0182421 A1 | 7/2009 | Silvestrini et al. |
| 2009/0209910 A1 | 8/2009 | Kugler et al. |
| 2009/0264813 A1 | 10/2009 | Chang |
| 2009/0287136 A1 | 11/2009 | Castillejos |
| 2010/0010416 A1 | 1/2010 | Juan, Jr. et al. |
| 2010/0087774 A1 | 4/2010 | Haffner et al. |
| 2010/0100104 A1 | 4/2010 | Yu et al. |
| 2010/0114006 A1 | 5/2010 | Baerveldt |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0191103 A1 | 7/2010 | Stamper et al. |
| 2010/0234790 A1 | 9/2010 | Tu et al. |
| 2010/0274258 A1 | 10/2010 | Silvestrini et al. |
| 2010/0274259 A1 | 10/2010 | Yaron et al. |
| 2010/0280317 A1 | 11/2010 | Silvestrini et al. |
| 2011/0009874 A1 | 1/2011 | Wardle et al. |
| 2011/0046536 A1 | 2/2011 | Stegmann et al. |
| 2011/0098627 A1 | 4/2011 | Wilcox |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123436 A1 | 5/2012 | Reitsamer et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2013/0149429 A1 | 6/2013 | Romoda et al. |
| 2013/0150770 A1 | 6/2013 | Horvath et al. |
| 2013/0245573 A1 | 9/2013 | de Juan, Jr. et al. |

FOREIGN PATENT DOCUMENTS

| | | |
|---|---|---|
| WO | WO 94/21205 A1 | 9/1994 |
| WO | WO 95/08310 A1 | 3/1995 |
| WO | WO 98/23237 | 6/1998 |
| WO | WO 02/074052 | 9/2002 |
| WO | WO-2007/087061 A2 | 8/2007 |
| WO | WO-2008/005873 A2 | 1/2008 |

OTHER PUBLICATIONS

Written Opinion in PCT application No. PCT/US2007/072547, mailed Dec. 31, 2008, 8 pages.
International Preliminary Report on Patentability in PCT application No. PCT/US2007/072547, mailed Jun. 1, 2009, 9 pages.
U.S. Appl. No. 12/964,298, filed Dec. 9, 2010, inventors Yu et al.
Quere, "Fluid Floating on a Fiber," Annu. Rev. Fluid Mech. 1999, 31:347-84.

* cited by examiner

METHODS FOR TREATING CLOSED ANGLE GLAUCOMA

FIELD OF THE INVENTION

The present invention generally relates to methods for treating closed angle glaucoma.

BACKGROUND

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

There are two main types of glaucoma, "open angle" and "closed angle" glaucoma. Open angle glaucoma refers to glaucoma cases in which intraocular pressure increases but an anterior chamber angle (drainage angle) of an eye remains open. A common cause of open angle glaucoma is blockage in the trabecular meshwork, the fluid flow pathways that normally drain aqueous humor from the anterior chamber of the eye. Closed angle glaucoma refers to glaucoma cases in which intraocular pressure increases due to partial or complete closure of the anterior chamber angle. In closed angle glaucoma, swelling or movement of the iris closes the anterior chamber angle and blocks fluid from accessing to the trabecular meshwork, which in turn obstructs outflow of the aqueous humor from the eye.

Generally, glaucoma may be treated by surgical intervention that involves placing a shunt in the eye to result in production of fluid flow pathways between the anterior chamber and various structures of the eye involved in aqueous humor drainage (e.g., Schlemm's canal or the subconjunctival space). Such fluid flow pathways allow for aqueous humor to exit the anterior chamber. Generally, the surgical intervention to implant the shunt involves inserting into the eye a deployment device that holds an intraocular shunt, and deploying the shunt from the device and into the eye. A deployment device holding the shunt enters the eye through a cornea (ab interno approach), and is advanced across the anterior chamber. The deployment device is advanced into the anterior chamber angle and through the sclera until a distal portion of the device is in proximity to a drainage structure of the eye. The shunt is then deployed from the deployment device, producing a conduit between the anterior chamber and various structures of the eye involved in aqueous humor drainage (e.g., Schlemm's canal, the sclera, or the subconjunctival space). See for example, Yu et al. (U.S. Pat. No. 6,544,249 and U.S. patent application number 2008/0108933) and Prywes (U.S. Pat. No. 6,007,511).

SUMMARY

A problem with treating closed angle glaucoma with surgical intervention is that the closed anterior chamber angle prevents an operator from advancing the deployment device into the anterior chamber angle, and thus the device cannot be properly positioned to deploy an intraocular shunt.

The present invention generally relates to methods for treating closed angle glaucoma that involve using a deployment device that is configured to both re-open a partially or completely closed anterior chamber angle and deploy an intraocular shunt. By re-opening the anterior chamber angle, the deployment device is provided access to the anterior chamber angle so that an operator may properly position the device to deploy the intraocular shunt, thereby generating a fluid flow pathway for outflow of aqueous humor from an anterior chamber of an eye.

In certain aspects, methods of the invention involve inserting into an eye a deployment device configured to hold an intraocular shunt, using the device to re-open an at least partially closed anterior chamber angle of an eye, and deploying the shunt from the device. Deploying the shunt results in a flow path from an anterior chamber of the eye to an area of lower pressure. Exemplary areas of lower pressure include intra-Tenon's space, the subconjunctival space, the episcleral vein, the suprachoroidal space, and Schlemm's canal. In certain embodiments, the area of lower pressure is the subarachnoid space.

In other aspects, methods of the invention involve inserting into an eye a deployment device configured to hold an intraocular shunt, advancing the device such that a protrusion on a distal end of the device advances into an at least partially closed anterior chamber angle of the eye, thereby re-opening the closed angle, and deploying the shunt from the device. In certain embodiments, a distal portion of the device includes a sleeve and a hollow shaft that is movable within the sleeve. In certain embodiments, the protrusion may be formed integrally with the distal end of the sleeve or may be connected to a distal end of the sleeve. In certain embodiments, the protrusion may surround the distal end of the sleeve, or the protrusion may extend around only a portion of the sleeve. In certain embodiments, the protrusion is a collar that surrounds the distal end of the sleeve. In other embodiments, the protrusion includes a flat bottom portion and an angled top portion. In particular embodiments, the angle of the top portion is substantially identical to an anterior chamber angle of an eye.

Methods of the invention are typically conducted using an ab interno approach. Such an approach is contrasted with an ab externo approach, which involves inserting a deployment device through the conjunctiva of the eye. Although, methods of the invention may be conducted using an ab externo approach.

Methods of the invention may be performed such that the distal portion of the deployment device is inserted above or below the corneal limbus. Methods of the invention may be performed such that the distal portion of the deployment device is inserted into the eye without removing an anatomical feature of the eye, such as the trabecular meshwork, the iris, the cornea, and the aqueous humor. In certain embodiments, methods of the invention may be conducted without substantial subconjunctival blebbing. In particular embodiments, methods of the invention are performed without the use of an optical apparatus that contacts the eye, such as a goniolens.

BRIEF DESCRIPTION OF THE DRAWINGS

FIG. 2B is a side view of the protrusion shown in FIG. 2A. FIG. 2C is a top view of the protrusion shown in FIG. 2A.

DETAILED DESCRIPTION

The present invention generally relates to methods for treating closed angle glaucoma that involve using a deployment device that is configured to both re-open a partially or completely closed anterior chamber angle and deploy an intraocular shunt. In certain aspects, methods of the invention involve inserting into an eye a deployment device configured to hold an intraocular shunt, using the device to re-open an at least partially closed anterior chamber angle of an eye, and deploying the shunt from the device.

Figure 1A:
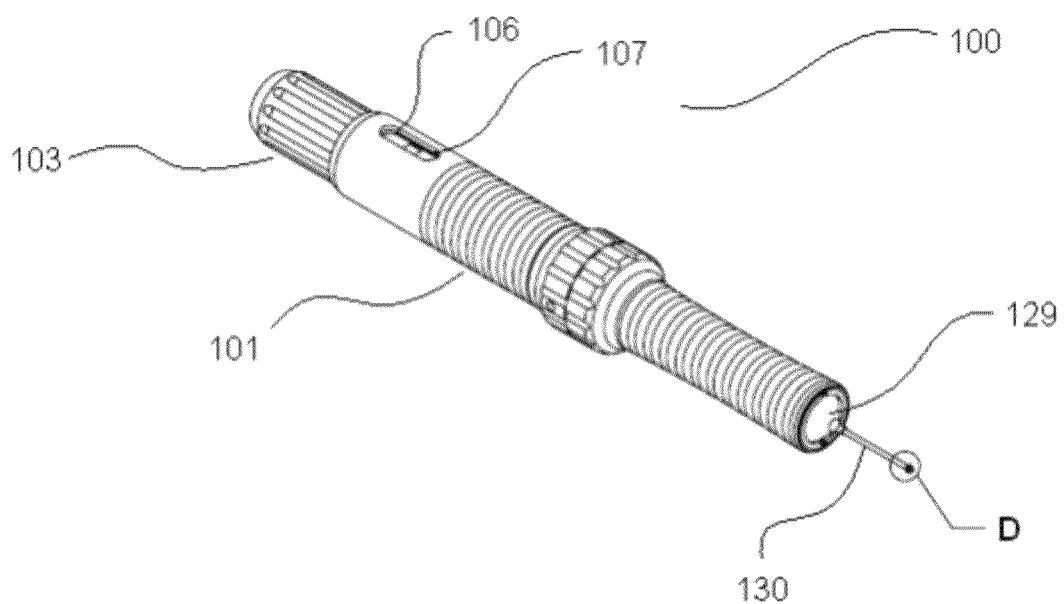
FIG. 1A is a schematic showing an embodiment of a shunt deployment device according to the invention.

Reference is now made to FIG. 1A which shows an embodiment of a shunt deployment device 100 that may be used to re-open a partially or completely closed anterior chamber angle and deploy an intraocular shunt. While FIG. 1 shows a handheld manually operated shunt deployment device, it will be appreciated that devices of the invention may be coupled with robotic systems and may be completely or partially automated. As shown in FIG. 1A deployment device 100 includes a generally cylindrical body or housing 101, however, the body shape of housing 101 could be other than cylindrical. Housing 101 may have an ergonomical shape, allowing for comfortable grasping by an operator. Housing 101 is shown with optional grooves 102 to allow for easier gripping by a surgeon.

Figure 1D:
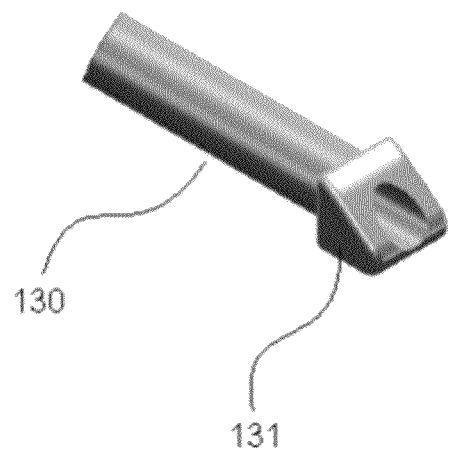
FIG. 1D is a schematic showing an enlarged view of a protrusion on a distal end of a distal portion of a housing of the device of FIG. 1A. In this figure, a bottom portion of the protrusion is flat and a top portion of the protrusion is angled.
Figure 1B:
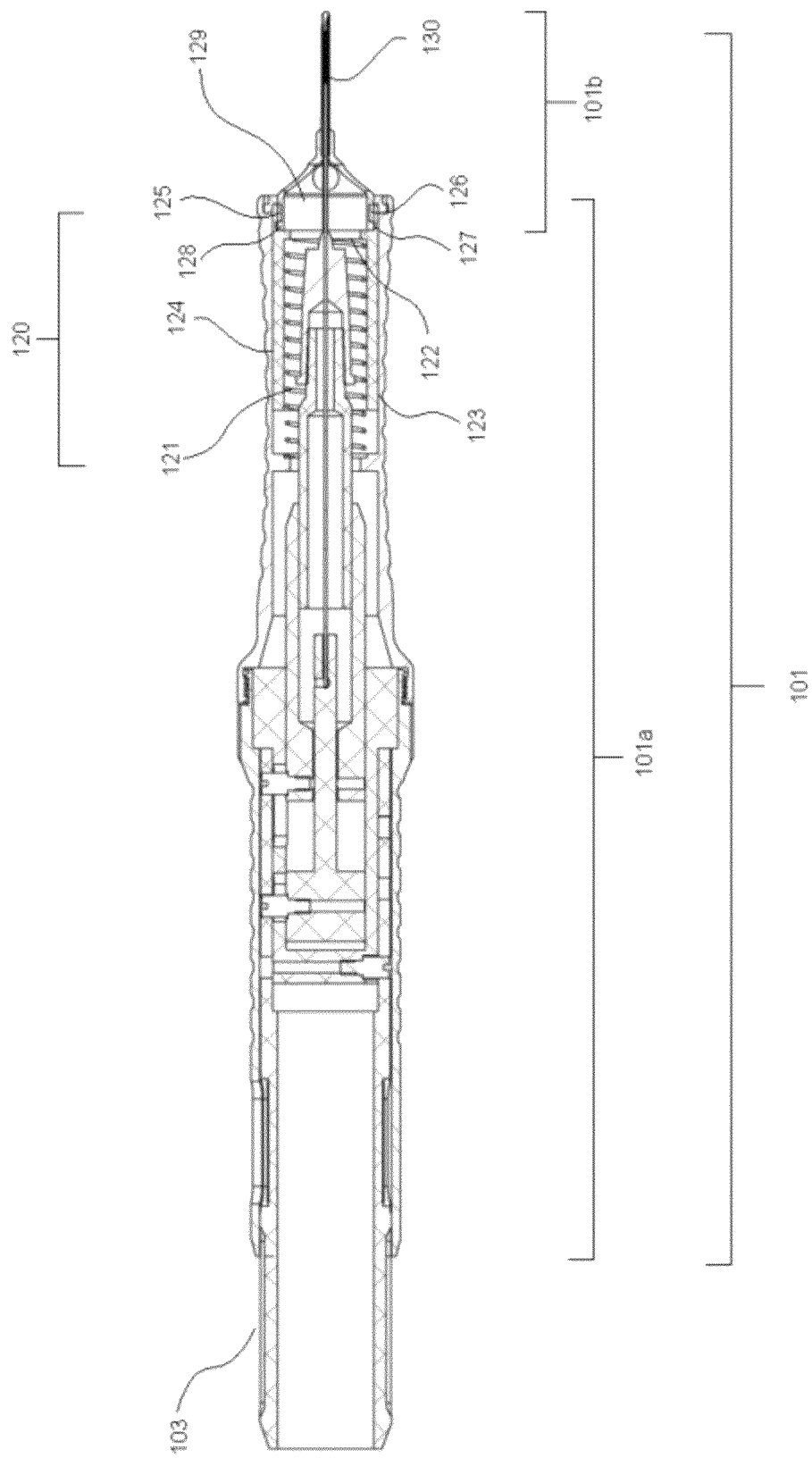
FIG. 1B shows a cross sectional view of the device of FIG. 1. In this figure, the distal portion of the housing is extended from the proximal portion of the housing.

FIG. 1B shows a cross sectional view of device 100. This figure shows that housing 101 includes a proximal portion 101a and a distal portion 101b. The distal portion 101b is movable within proximal portion 101a. In this figure, spring mechanism 120 includes a spring 121 that controls movement of distal portion 101b. Spring mechanism 120 further includes a member 122 that acts as a stopper and limits axial retraction of distal portion 101b within proximal portion 101a. Spring mechanism 120 further includes members 123 and 124 that run the length of spring 121. The ends of members 123 and 124 include flanges 125 and 126 that project inward from members 123 and 124. An end of distal portion 101b includes flanges 127 and 128 that project outward from distal portion 101b. Flanges 125 and 126 interact with flanges 127 and 128 to prevent release of distal portion 101b from proximal portion 101a. The flanges 125 and 126 and 127 and 128 hold the distal portion 101b in an extended position until a compressive force acts upon distal portion 101b, thereby causing distal portion 101b to partially retract within proximal portion 101a.

Figure 1C:
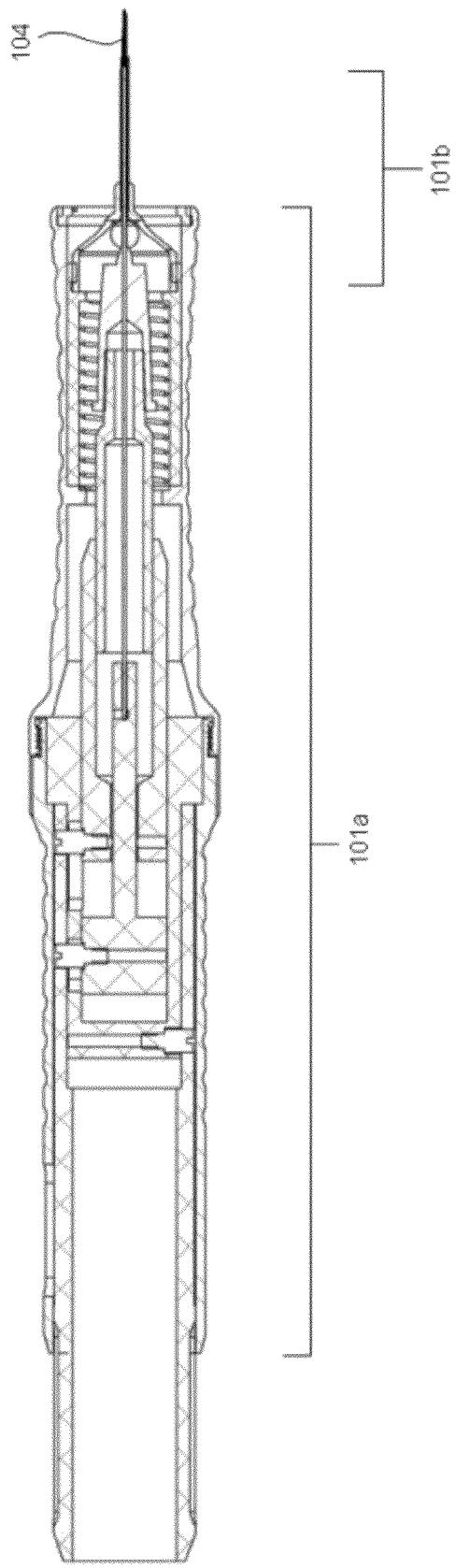
FIG. 1C shows a cross sectional view of the device of FIG. 1. In this figure, the distal portion of the housing is retracted within the proximal portion of the housing.

Distal portion 101b includes a capsule 129 and a hollow sleeve 130. Capsule 129 and sleeve 130 may be formed integrally or may be separate components that are coupled or connected to each other. The hollow sleeve 130 is configured for insertion into an eye and to extend into an anterior chamber of an eye. FIG. 1B shows distal portion 101b of housing 101 extended from proximal portion 101a of housing 101. In this configuration, hollow shaft 104 (not shown in this figure) is completely disposed within sleeve 130. FIG. 1C shows distal portion 101b of housing 101 retracted within proximal portion 101a of housing 101. Retraction of distal portion 101b of housing 101 within proximal portion 101a of housing 101 exposes hollow shaft 104, which is discussed in greater detail below.

A distal end of sleeve 130 includes a protrusion 131 (FIG. 1D). Protrusion 131 is of a shape and size that it is capable of re-opening a partially or completely closed anterior chamber angle of an eye as an operator is advancing the device 100 through an anterior chamber of an eye. In a standard ab interno approach (see for example Yu et al. U.S. Pat. No. 6,544,249 and U.S. patent application number. 2008/0108933) a deployment device holding a shunt enters an eye through a cornea. The deployment device is advanced across the anterior chamber in what is referred to as a transpupil implant insertion. The deployment device is advanced into the anterior chamber angle on the opposite side of the eye from which the device entered the eye. With devices of the invention, upon advancement of the device 100 across an anterior chamber of the eye, the protrusion 131 at the distal end of the hollow sleeve 130 will contact a partially or completely closed anterior chamber angle, and continued advancement of the device 100 will result in the protrusion 131 re-opening the partially or completely closed anterior chamber angle. Once re-opened by the protrusion 131, the device 100 can be moved into proper position for exposure of the hollow shaft 104, which will advance through the sclera for deployment of an intraocular shunt. The protrusion 131, provides adequate surface area at the distal end of sleeve 130, thus preventing sleeve 130 from entering the tissue of the eye that is blocking access the trabecular meshwork (e.g., the iris).

Figure 2A:
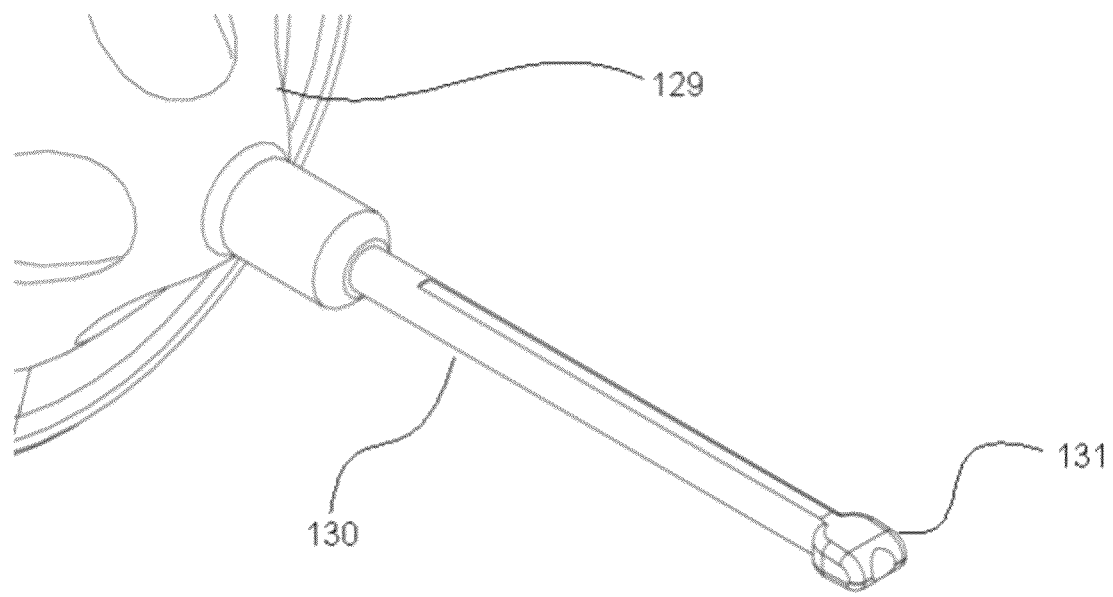
FIGS. 2A-2C are schematics showing an enlarged view of a protrusion on a distal end of a distal portion of a housing of devices of the invention.
Figure 2B:
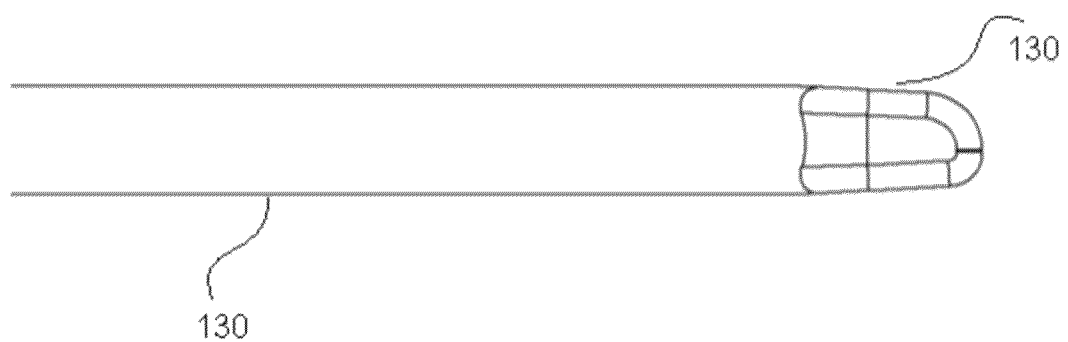
Figure 2C:
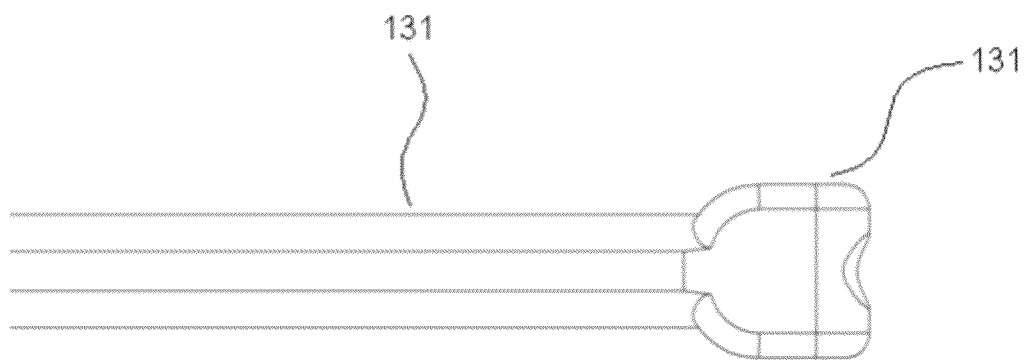
Figure 3:
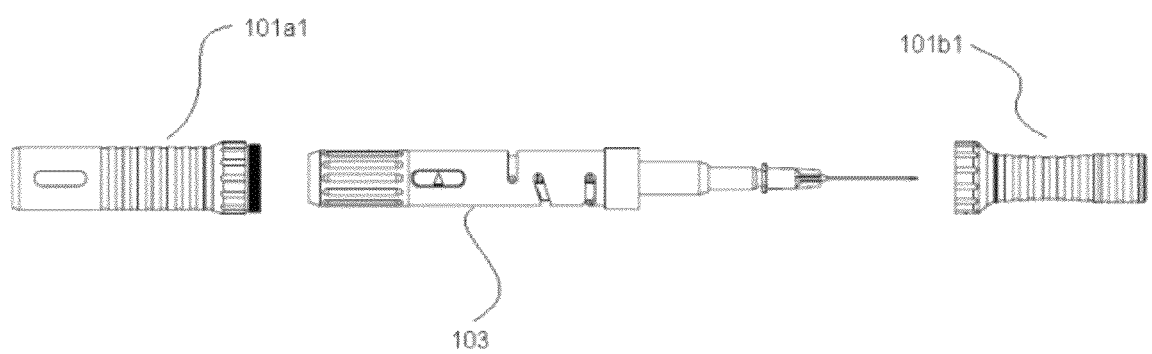
FIG. 3 shows an exploded view of the device shown in FIG. 1.
Figure 4A:
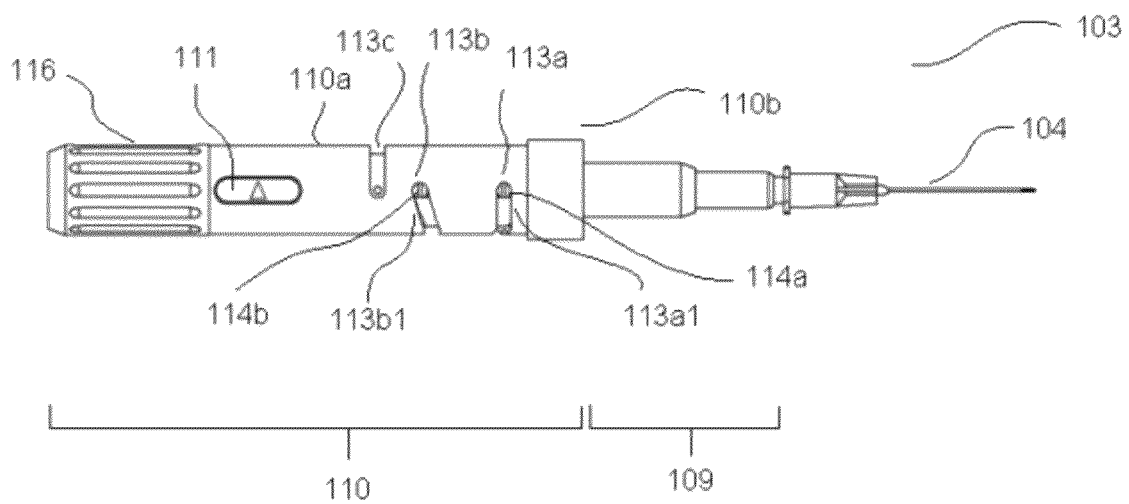
FIGS. 4A to 4D are schematics showing different enlarged views of the deployment mechanism of the deployment device.
Figure 4B:
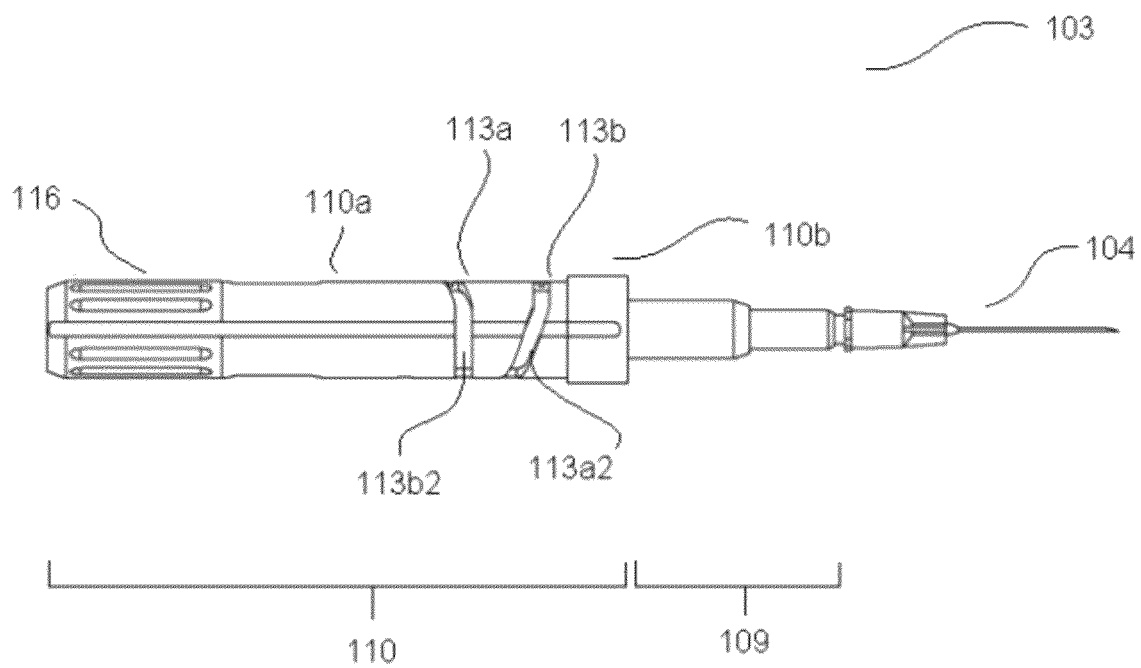
Figure 4C:
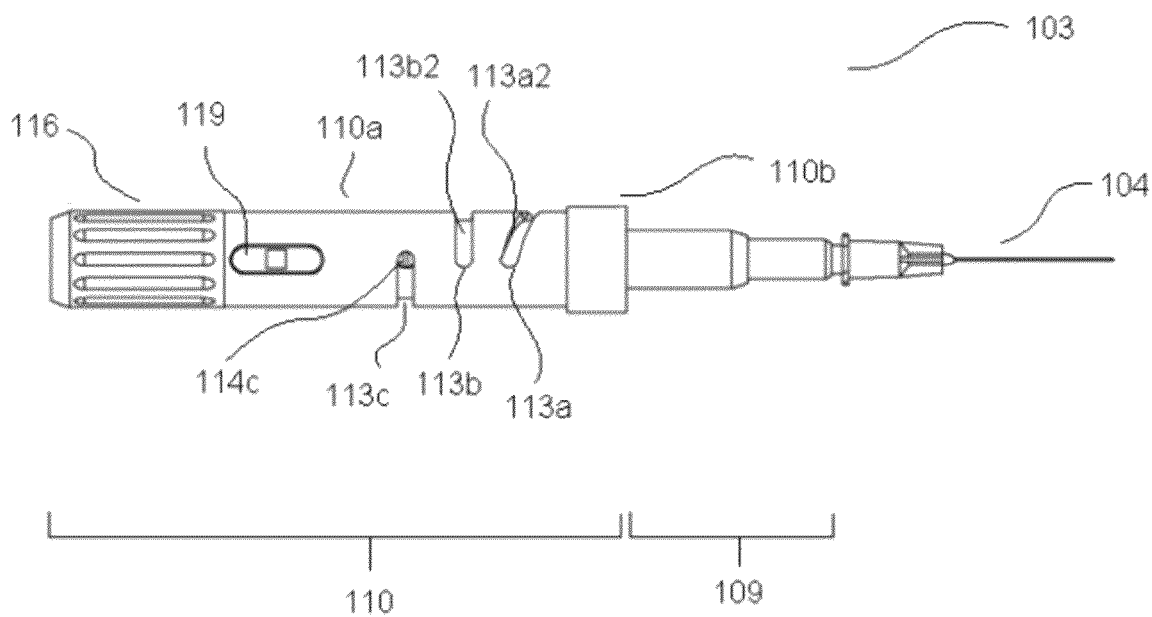
Figure 4D:
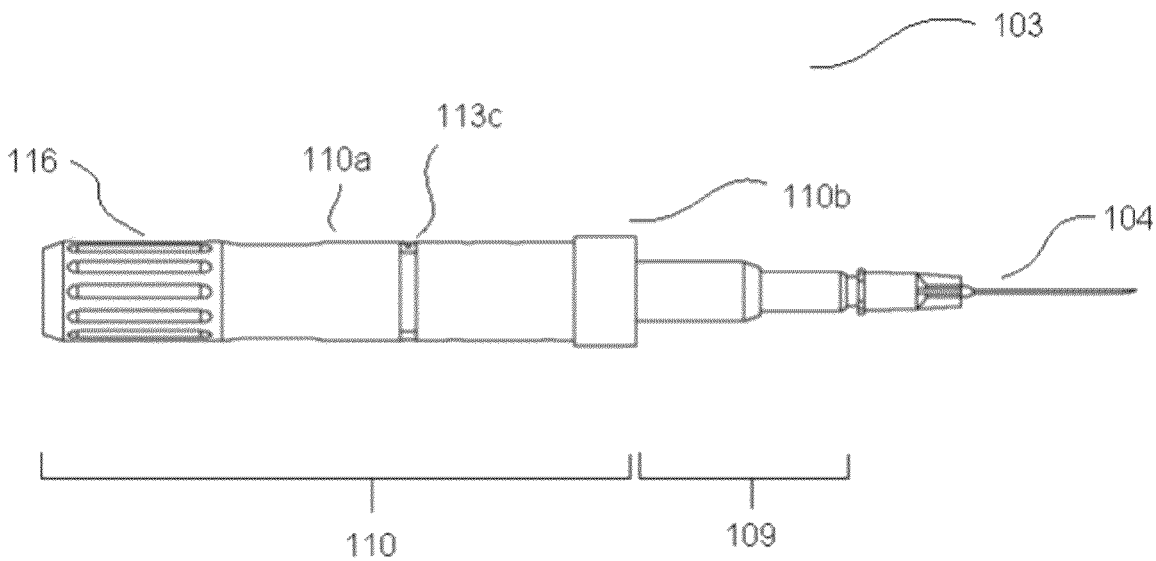

In certain embodiments, protrusion 131 has a substantially flat bottom portion and an angled top portion (FIG. 1D). In other embodiments, protrusion 131 has a slightly tapered top and a slightly tapered bottom with a rounded distal portion (FIGS. 2A-2C). Referring back to FIG. 1D, the angle of the top portion is substantially identical to an anterior chamber angle of an eye. Such a shape of the protrusion ensures that the device of the invention will conform and easily slide into the anterior chamber angle of the eye, the place for proper deployment of an intraocular shunt.

Referring back to FIG. 1A, the proximal portion 101a of the housing 101 is open at its proximal end, such that a portion of a deployment mechanism 103 may extend from the proximal end of the proximal portion 101a of the housing 101. The sleeve 130 of the distal portion 101b of the housing 101 is also open such that at least a portion of a hollow shaft 104 may extend inside the housing, into sleeve 130 of the distal portion 101b of the housing 101, and extend beyond the distal end of the sleeve 130 in certain configurations (such as the deployment configuration). Housing 101 further includes a slot 106 through which an operator, such as a surgeon, using the device 100 may view an indicator 107 on the deployment mechanism 103.

Housing 101 and protrusion 131 may be made of any material that is suitable for use in medical devices. For example, housing 101 and protrusion 131 may be made of a lightweight aluminum or a biocompatible plastic material. Examples of such suitable plastic materials include polycarbonate and other polymeric resins such as DELRIN and ULTEM. In certain embodiments, housing 101 and protrusion 131 are made of a material that may be autoclaved, and thus allow for housing 101 and protrusion 131 to be re-usable. Alternatively, device 100, may be sold as a one-time-use device, and thus the material of the housing and the protrusion does not need to be a material that is autoclavable.

The proximal portion 101a of housing 101 may be made of multiple components that connect together to form the housing. FIG. 4 shows an exploded view of deployment device 100. In this figure, proximal portion 101a of housing 101, is shown having two components 101a1 and 101a2. The components are designed to screw together to form proximal portion 101a of housing 101. FIG. 4 also shows deployment mechanism 103. The housing 101 is designed such that deployment mechanism 103 fits within assembled housing 101. Housing 101 is designed such that components of deployment mechanism 103 are movable within housing 101.

FIGS. 4A to 4D show different enlarged views of the deployment mechanism 103. Deployment mechanism 103 may be made of any material that is suitable for use in medical devices. For example, deployment mechanism 103 may be made of a lightweight aluminum or a biocompatible plastic material. Examples of such suitable plastic materials include polycarbonate and other polymeric resins such as DELRIN and ULTEM. In certain embodiments, deployment mechanism 103 is made of a material that may be autoclaved, and thus allow for deployment mechanism 103 to be re-usable. Alternatively, device 100 may be sold as a one-time-use device, and thus the material of the deployment mechanism does not need to be a material that is autoclavable.

Deployment mechanism 103 includes a proximal portion 109 and a distal portion 110. The deployment mechanism 103 is configured such that proximal portion 109 is movable within distal portion 110. More particularly, proximal portion 109 is capable of partially retracting to within distal portion 110.

In this embodiment, the proximal portion 109 is shown to taper to a connection with a hollow shaft 104. This embodiment is illustrated such that the connection between the hollow shaft 104 and the proximal portion 109 of the deployment mechanism 103 occurs inside the housing 101. Hollow shaft 104 may be removable from the proximal portion 109 of the deployment mechanism 103. Alternatively, the hollow shaft 104 may be permanently coupled to the proximal portion 109 of the deployment mechanism 103.

Figure 6:
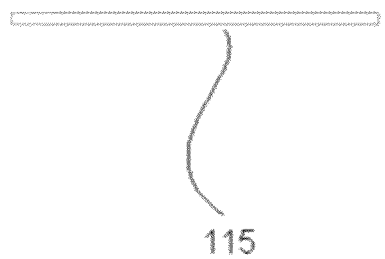
FIG. 6 depicts a schematic of an exemplary intraocular shunt.

Generally, hollow shaft 104 is configured to hold an intraocular shunt 115. An exemplary intraocular shunt 115 in shown in FIG. 6. Other exemplary intraocular shunts are shown in Yu et al. (U.S. patent application number 2008/0108933). Generally, in one embodiment, intraocular shunts are of a cylindrical shape and have an outside cylindrical wall and a hollow interior. The shunt may have an inner diameter of approximately 50 µm to approximately 250 µm, an outside diameter of approximately 190 µm to approximately 300 µm, and a length of approximately 0.5 mm to about 20 mm. Thus, hollow shaft 104 is configured to at least hold a shunt of such shape and such dimensions. However, hollow shaft 104 may be configured to hold shunts of different shapes and different dimensions than those described above, and the invention encompasses a shaft 104 that may be configured to hold any shaped or dimensioned intraocular shunt. In particular embodiments, the shaft has an inner diameter of approximately 200 µm to approximately 400 µm.

The shaft 104 may be any length. A usable length of the shaft may be anywhere from about 5 mm to about 40 mm, and is 15 mm in certain embodiments. In certain embodiments, the shaft is straight. In other embodiments, shaft 104 is of a shape other than straight, for example a shaft having a bend along its length or a shaft having an arcuate portion. Exemplary shaped shafts are shown for example in Yu et al. (U.S. patent application number 2008/0108933). In particular embodiments, the shaft includes a bend at a distal portion of the shaft. In other embodiments, a distal end of the shaft is beveled or is sharpened to a point.

The shaft 104 may hold the shunt at least partially within the hollow interior of the shaft 104. In other embodiments, the shunt is held completely within the hollow interior of the shaft 104. Alternatively, the hollow shaft may hold the shunt on an outer surface of the shaft 104. In particular embodiments, the shunt is held within the hollow interior of the shaft 104. In certain embodiments, the hollow shaft is a needle having a hollow interior. Needles that are configured to hold an intraocular shunt are commercially available from Terumo Medical Corp. (Elkington, Md.).

A distal portion of the deployment mechanism 103 includes optional grooves 116 to allow for easier gripping by an operator for easier rotation of the deployment mechanism, which will be discussed in more detail below. The distal portion 110 of the deployment mechanism also includes at least one indicator that provides feedback to an operator as to the state of the deployment mechanism. The indicator may be any type of indicator know in the art, for example a visual indicator, an audio indicator, or a tactile indicator. FIG. 4 shows a deployment mechanism having two indicators, a ready indicator 111 and a deployed indicator 119. Ready indicator 111 provides feedback to an operator that the deployment mechanism is in a configuration for deployment of an intraocular shunt from the deployment device 100. The indicator 111 is shown in this embodiment as a green oval having a triangle within the oval. Deployed indicator 119 provides feedback to the operator that the deployment mechanism has been fully engaged and has deployed the shunt from the deployment device 100. The deployed indicator 119 is shown in this embodiment as a yellow oval having a black square within the oval. The indicators are located on the deployment mechanism such that when assembled, the indicators 111 and 119 may be seen through slot 106 in housing 101.

Figure 5A:
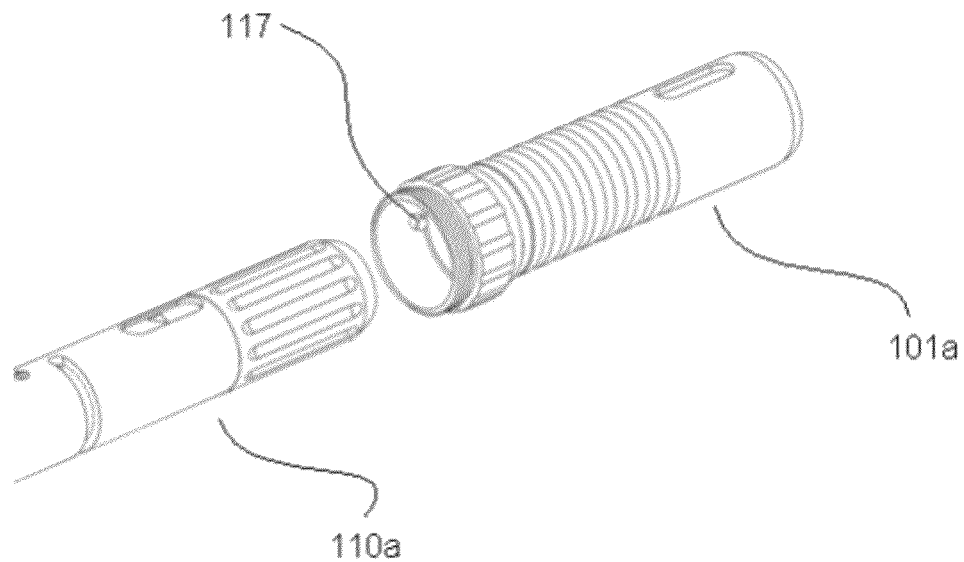
FIGS. 5A to 5C are schematics showing interaction of the deployment mechanism with a portion of the housing of the deployment device.
Figure 5B:
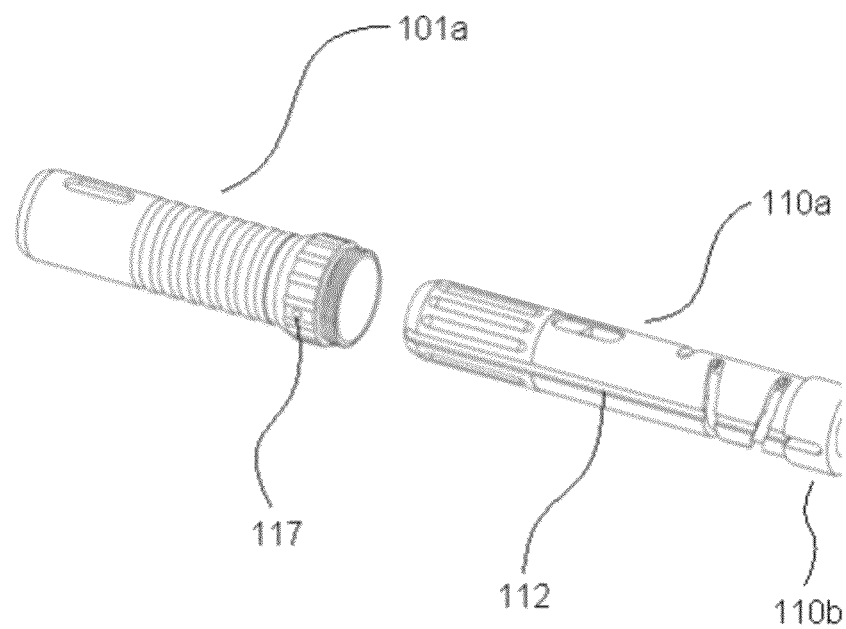
Figure 5C:
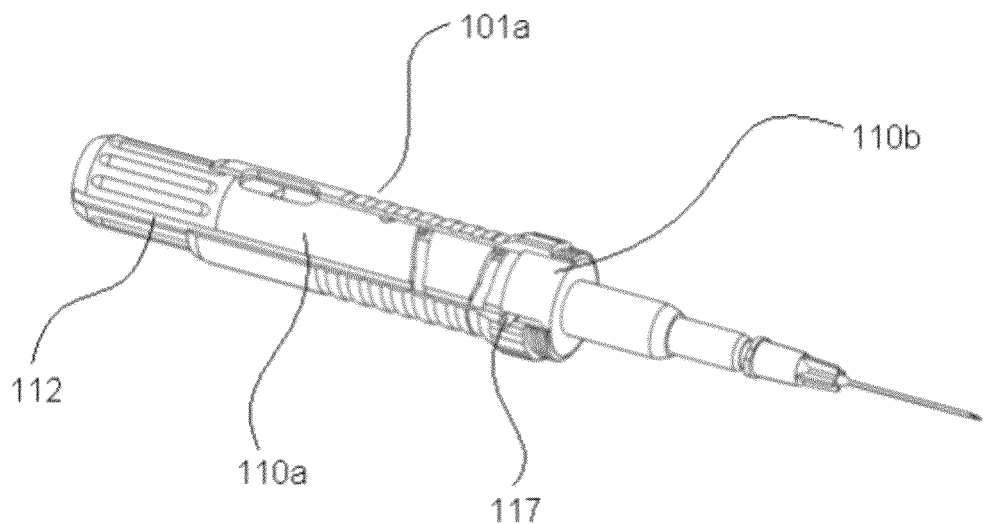

The distal portion 110 includes a stationary portion 110b and a rotating portion 110a. The distal portion 110 includes a channel 112 that runs part of the length of stationary portion 110b and the entire length of rotating portion 110a. The channel 112 is configured to interact with a protrusion 117 on an interior portion of housing component 101a (FIGS. 5A and 5B). During assembly, the protrusion 117 on housing component 101a1 is aligned with channel 112 on the stationary portion 110b and rotating portion 110a of the deployment mechanism 103. The distal portion 110 of deployment mechanism 103 is slid within housing component 101a1 until the protrusion 117 sits within stationary portion 110b (FIG. 5C). Assembled, the protrusion 117 interacts with the stationary portion 110b of the deployment mechanism 103 and prevents rotation of stationary portion 110b. In this configuration, rotating portion 110a is free to rotate within housing component 101a1.

Referring back to FIG. 4, the rotating portion 110a of distal portion 110 of deployment mechanism 103 also includes channels 113a, 113b, and 113c. Channel 113a includes a first portion 113a1 that is straight and runs perpendicular to the length of the rotating portion 110a, and a second portion 113a2 that runs diagonally along the length of rotating portion 110a, downwardly toward a distal end of the deployment mechanism 103. Channel 113b includes a first portion 113b1 that runs diagonally along the length of the rotating portion 110a, upwardly toward a proximal end of the deployment mechanism 103, and a second portion that is straight and runs perpendicular to the length of the rotating portion 110a. The point at which first portion 113a1 transitions to second portion 113a2 along channel 113a, is the same as the point at which first portion 113b1 transitions to second portion 113b2 along channel 113b. Channel 113c is straight and runs perpendicular to the length of the rotating portion 110a. Within each of channels 113a, 113b, and 113c, sit members 114a, 114b, and 114c respectively. Members 114a, 114b, and 114c are movable within channels 113a, 113b, and 113c. Members 114a, 114b, and 114c also act as stoppers that limit movement of rotating portion 110a, which thereby limits axial movement of the shaft 104.

Figure 7:
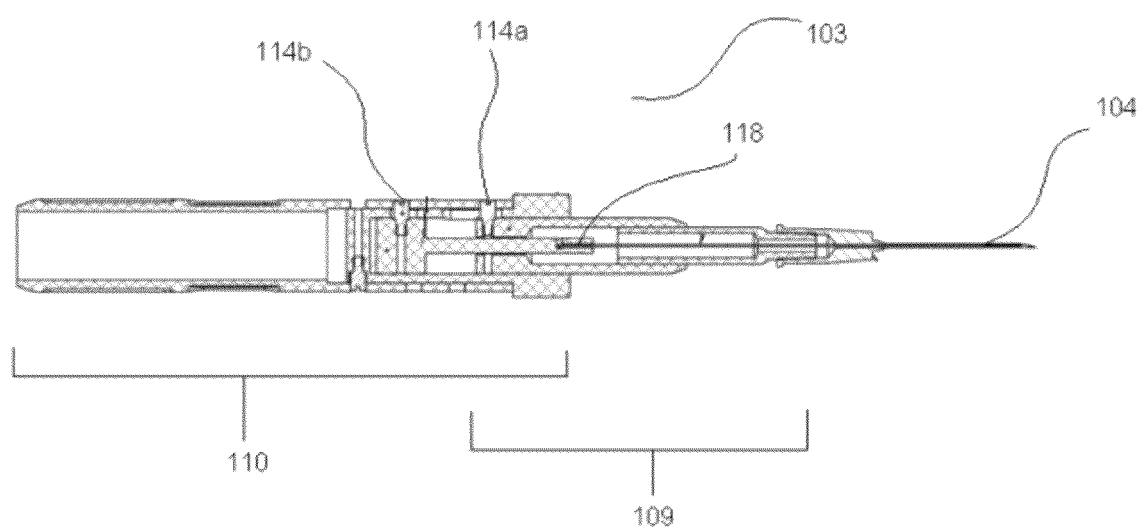
FIG. 7 shows a cross sectional view of the deployment mechanism of the deployment device.

FIG. 7 shows a cross-sectional view of deployment mechanism 103. Member 114a is connected to the proximal portion 109 of the deployment mechanism 103. Movement of member 114a results in retraction of the proximal portion 109 of the deployment mechanism 103 to within the distal portion 110 of the deployment mechanism 103. Member 114b is connected to a pusher component 118. The pusher component 118 extends through the proximal portion 109 of the deployment mechanism 103 and extends into a portion of hollow shaft 104. The pusher component is involved in deployment of a shunt from the hollow shaft 104. An exemplary pusher component is a plunger. Movement of member 114b engages pusher 118 and results in pusher 118 advancing within hollow shaft 104.

Reference is now made to FIGS. 8-14, which accompany the following discussion regarding deployment of a shunt 115 from deployment device 100. FIG. 8A shows deployment device 100 is a pre-deployment or insertion configuration. In this configuration, shunt 115 is loaded within hollow shaft 104 (FIG. 8B). As shown in FIG. 8B, shunt 115 is only partially within shaft 104, such that a portion of the shunt is exposed. However, the shunt 115 does not extend beyond the end of the shaft 104. In other embodiments, the shunt 115 is completely disposed within hollow shaft 104. The shunt 115 is loaded into hollow shaft 104 such that the shunt abuts pusher component 118 within hollow shaft 104.

Figure 8A:
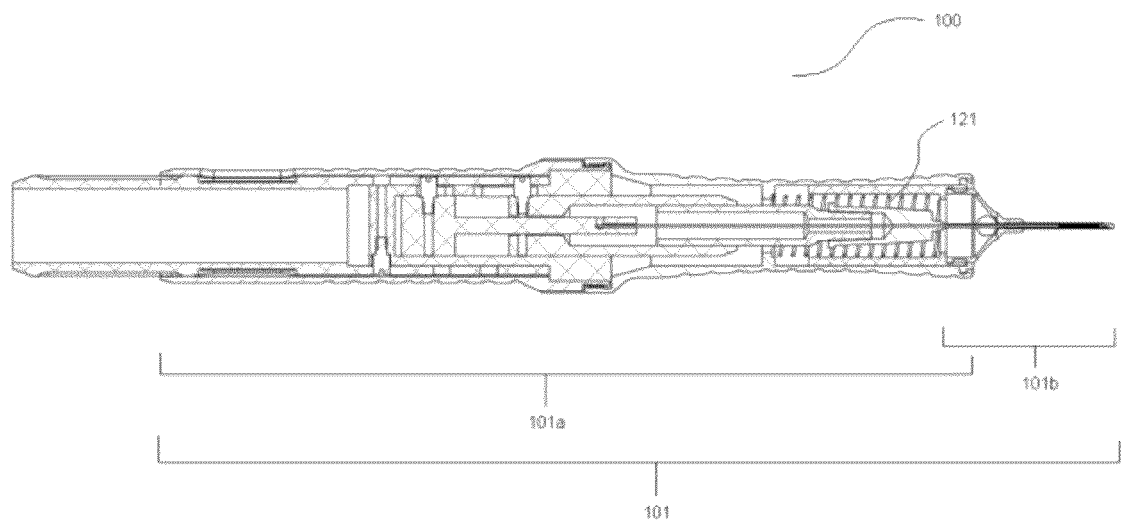
FIG. 8A is a schematic showing deployment devices of the invention in a pre-deployment or insertion configuration.
Figure 8B:
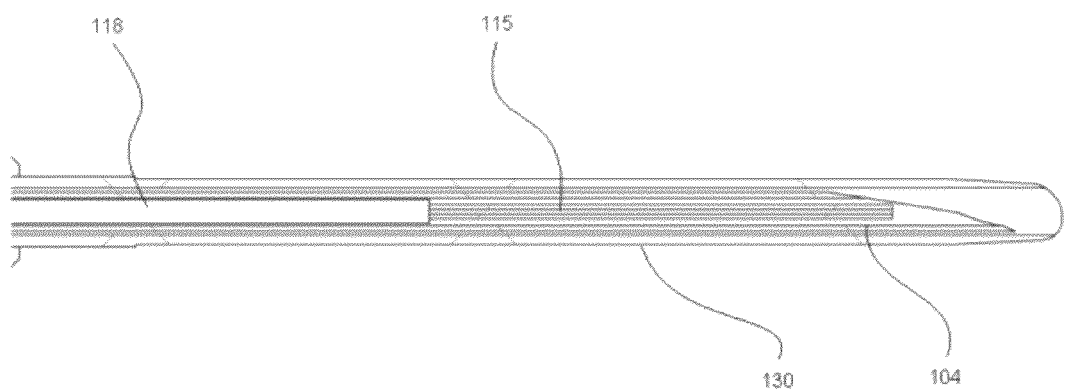
FIG. 8B shows an enlarged view of the distal portion of the deployment device of FIG. 8A. This figure shows an intraocular shunt loaded within a hollow shaft of the deployment device and that the shaft is completely disposed within the sleeve of the housing.

In the pre-deployment or insertion configuration, the distal portion 101b of the housing 101 is in an extended position, with spring 121 in a relaxed state (FIG. 8A). Additionally, in the pre-deployment configuration, the shaft 104 is fully disposed within the sleeve 130 of the distal portion 101b of the housing 101 (FIG. 8B). Pusher 118 abuts shunt 115 (FIG. 8B).

Figure 8C:
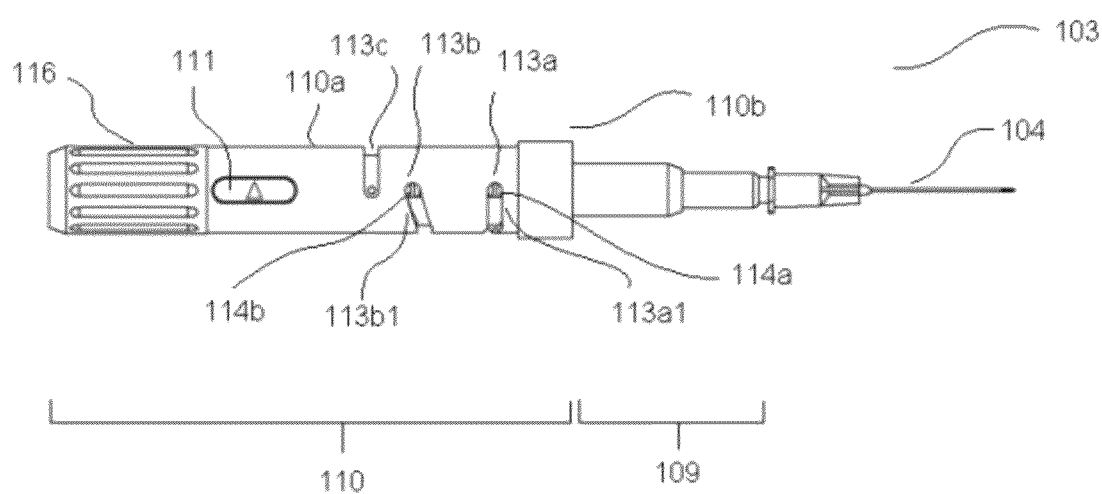
FIG. 8C show a schematic of the deployment mechanism in a pre-deployment or insertion configuration.
Figure 8D:
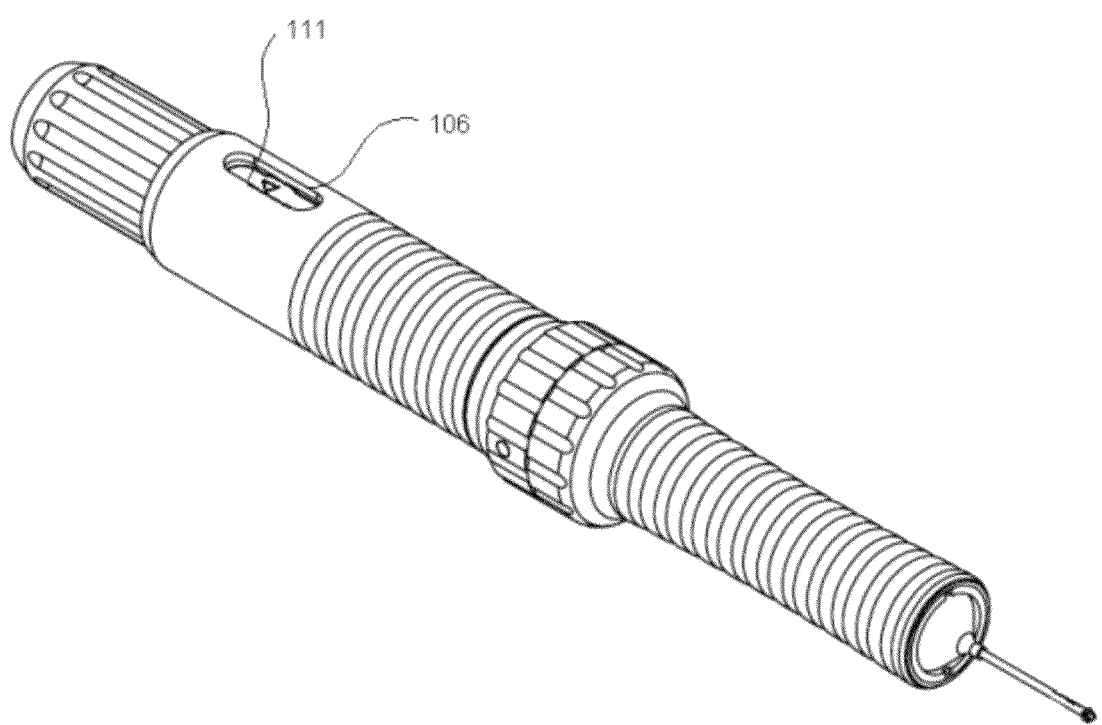
FIG. 8D is another schematic showing deployment devices of the invention in a pre-deployment or insertion configuration.

The deployment mechanism 103 is configured such that member 114a abuts a proximal end of the first portion 113a1 of channel 113a, and member 114b abut a proximal end of the first portion 113b1 of channel 113b (FIG. 8C). In this configuration, the ready indicator 111 is visible through slot 106 of the housing 101, providing feedback to an operator that the deployment mechanism is in a configuration for deployment of an intraocular shunt from the deployment device 100 (FIG. 8D). In this configuration, the device 100 is ready for insertion into an eye (insertion configuration or pre-deployment configuration).

Figure 9:
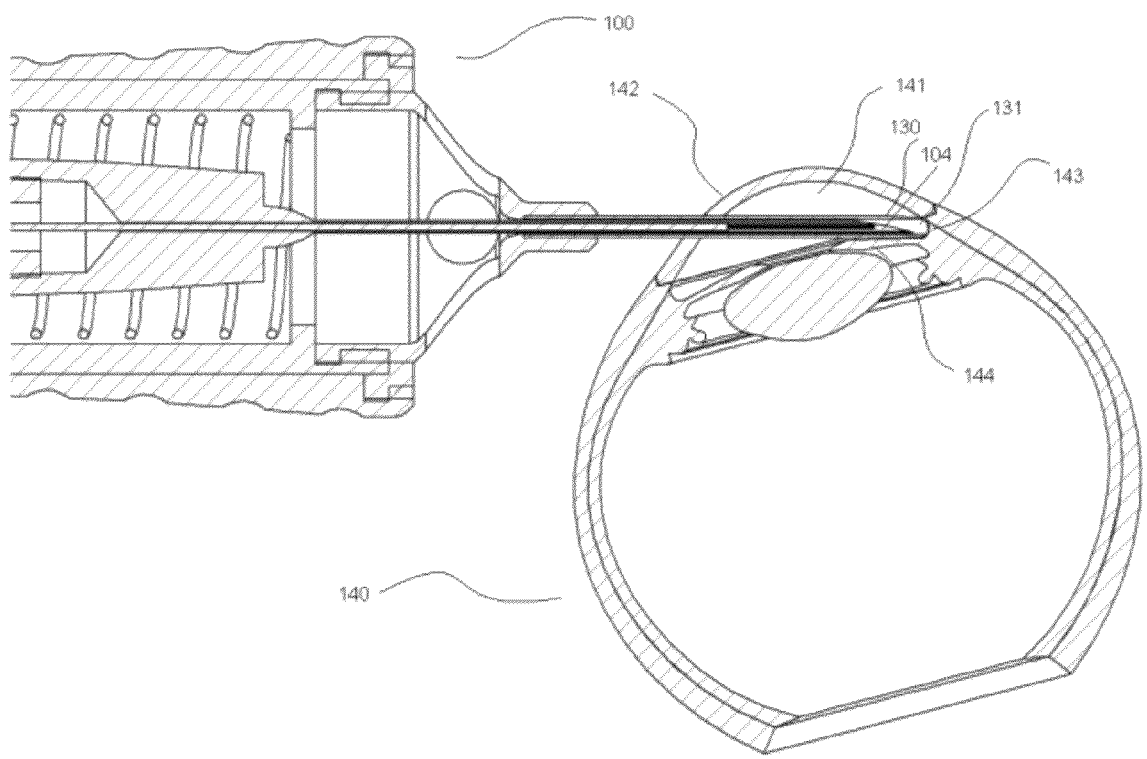
FIG. 9 is a schematic showing insertion of a device of the invention into an anterior chamber of the eye. This figure also shows the sleeve and protrusion fitted within an anterior chamber angle of the eye.

FIG. 9 shows device 100 in the insertion configuration and inserted into an eye 140. Any of a variety of methods known in the art may be used to insert devices of the invention into an eye. In certain embodiments, devices of the invention may be inserted into the eye using an ab externo approach (entering through the conjunctiva) or an ab interno approach (entering through the cornea). In particular embodiment, the approach is an ab interno approach as shown Yu et al. (U.S. Pat. No. 6,544,249 and U.S. patent application number 2008/0108933) and Prywes (U.S. Pat. No. 6,007,511), the content of each of which is incorporated by reference herein in its entirety.

FIG. 9 shows an ab interno approach for insertion of device 100 into the eye 140. In this figure, protrusion 131 at the distal end of the sleeve 130 has been advanced across the anterior chamber 141 to the anterior chamber angle 143 on the opposite side of the eye 140 from which the device entered the eye 140. FIG. 9 shows protrusion 131 and sleeve 130 fitted within the anterior chamber angle 143 of the eye 140, thus re-opening the partially or completely closed anterior chamber angle 143.

In certain embodiments, such insertion and placement is accomplished without the use of an optical apparatus that contacts the eye, such as a goniolens. In certain embodiments this insertion is accomplished without the use of any optical apparatus. Insertion without the use of an optical apparatus that contacts the eye, or any optical apparatus, is possible because of various features of the device described discussed herein. The shape of the protrusion 131 is such that it corrects for an insertion angle that is too steep or too shallow, ensuring that the sleeve 130 is fitted into the anterior chamber angle of the eye, the place for proper deployment of an intraocular shunt. Further, the shape of the protrusion provides adequate surface area at the distal end of sleeve 130 to prevent enough force from being generated at the distal end of sleeve 130 that would result in sleeve 130 entering an improper portion of the sclera 142 (if the insertion angle is too shallow) or entering an improper portion of the iris 144 (if the insertion angle is too steep). Additionally, since the shaft 104 is fully disposed within the sleeve 130, it cannot piece tissue of the eye until it is extended from the sleeve 130. Thus, if the insertion angle is too shallow or too steep, the protrusion 131 can cause movement and repositioning of the sleeve 130 so that the sleeve 130 is properly positioned to fit in the anterior chamber angle of the eye for proper deployment of the shunt. Due to these features of device 100, devices of the invention provide for deploying intraocular shunts without use of an optical apparatus that contacts the eye, preferably without use of any optical apparatus.

Figure 10:
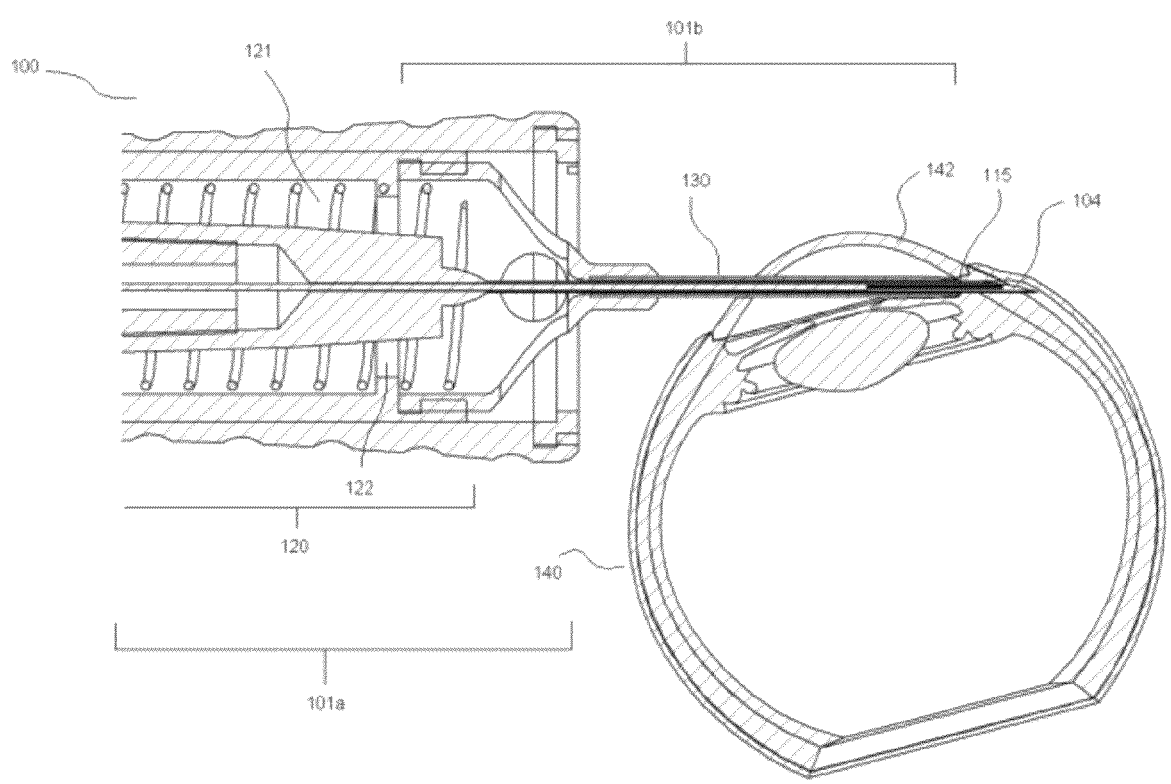
FIG. 10 is a schematic showing extension of the shaft from within the sleeve, which is accomplished by partial retraction of the distal portion of housing to within the proximal portion of housing.

Once the device has been inserted into the eye and the protrusion 131 and the sleeve 130 are fitted within the anterior chamber angle of the eye, the hollow shaft 104 may be extended from within the sleeve 130. Referring now to FIG. 10 which shows extension of the shaft 104 from within the sleeve 130, which is accomplished by partial retraction of distal portion 101b of housing 101 to within proximal portion 101a of housing 101.

Retraction of the distal portion 101b of housing 101 to within proximal portion 101a of housing 101 is accomplished by an operator continuing to apply force to advance device 100 after the protrusion 131 and the sleeve 130 are fitted within the anterior chamber angle of the eye. The surface area of protrusion 131 prevents the application of the additional force by the operator from advancing sleeve 130 into the sclera 134. Rather, the additional force applied by the operator results in engagement of spring mechanism 120 and compression of spring 121 within spring mechanism 120. Compression of spring 120 results in retraction of distal portion 101b of housing 101 to within proximal portion 101a of housing 101. The amount of retraction of distal portion 101b of housing 101 to within proximal portion 101a of housing 101 is limited by member 122 that acts as a stopper and limits axial retraction of distal portion 101b within proximal portion 101a.

Retraction of distal portion 101b of housing 101 to within proximal portion 101a of housing 101 results in extension of hollow shaft 104, which now extends beyond the distal end of sleeve 130 and advances through the sclera 142 to an area of lower pressure than the anterior chamber. Exemplary areas of lower pressure include Schlemm's canal, the subconjunctival space, the episcleral vein, the suprachoroidal space, or the intra-Tenon's space.

In this figure, a distal end of the shaft is shown to be located within the intra-Tenon's space. Within an eye, there is a membrane known as the conjunctiva, and the region below the conjunctiva is known as the subconjunctival space. Within the subconjunctival space is a membrane known as Tenon's capsule. Below Tenon's capsule there are Tenon's adhesions that connect the Tenon's capsule to the sclera. The space between Tenon's capsule and the sclera where the Tenon's adhesions connect the Tenon's capsule to the sclera is known as the intra-Tenon's space. This figure is exemplary and depicts only one embodiment for a location of lower pressure. It will be appreciated that devices of the invention may deploy shunts to various different locations of the eye and are not limited to deploying shunts to the intra-Tenon's space is shown by way of example in this figure. In this configuration, the shunt 115 is still completely disposed within the shaft 104.

The distal end of shaft 104 may be beveled to assist in piercing the sclera and advancing the distal end of the shaft 104 through the sclera. In this figure, the distal end of the shaft 104 is shown to have a double bevel (See also FIG. 8B). The double bevel provides an angle at the distal end of the shaft 104 such that upon entry of the shaft into intra-Tenon's space, the distal end of shaft 104 will by parallel with Tenon's capsule and will thus not pierce Tenon's capsule and enter the subconjunctival space. This ensures proper deployment of the shunt such that a distal end of the shunt 115 is deployed within the intra-Tenon's space, rather than deployment of the distal end of the shunt 115 within the subconjunctival space. Changing the angle of the bevel allows for placement of shunt 115 within other areas of lower pressure than the anterior chamber, such as the subconjunctival space. It will be understood that FIG. 11 is merely one embodiment of where shunt 115 may be placed within the eye, and that devices of the invention are not limited to placing shunts within intra-Tenon's space and may be used to place shunts into many other areas of the eye, such as Schlemm's canal, the subconjunctival space, the episcleral vein, or the suprachoroidal space.

Figure 11A:
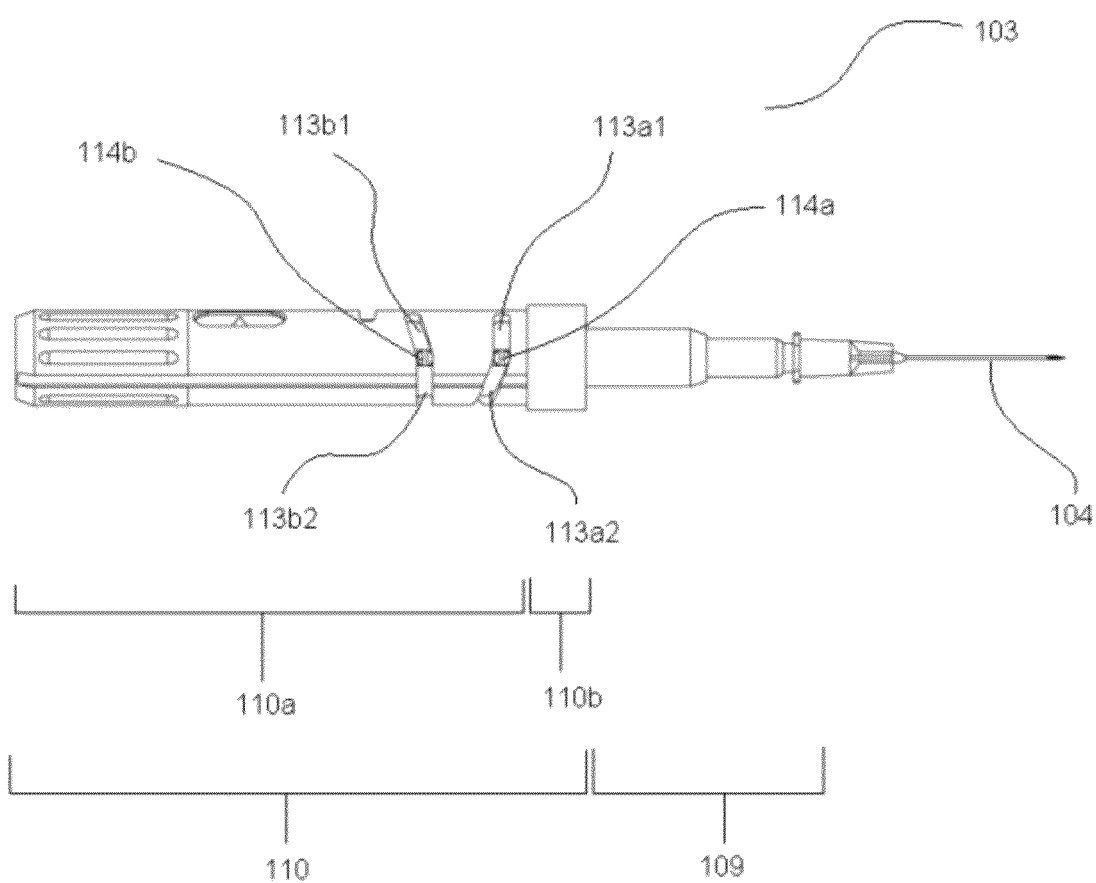
FIGS. 11A and 11B show schematics of the deployment mechanism at the end of the first stage of deployment of the shunt from the deployment device.
Figure 11:
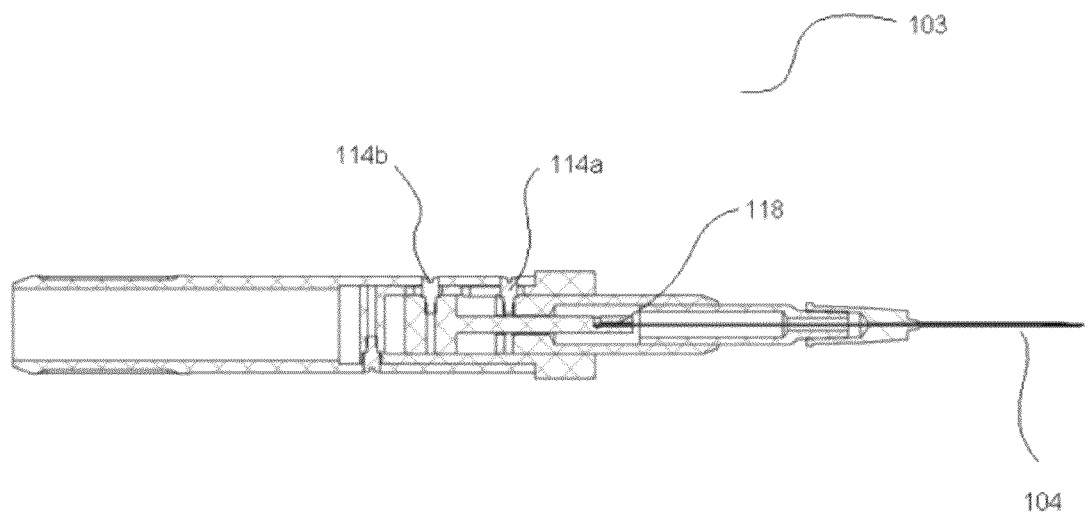
FIG. 11C shows an enlarged view of the distal portion of the deployment device of FIG. 11A. This figure shows an intraocular shunt partially deployed from within a hollow shaft of the deployment device.
Figure 11C:
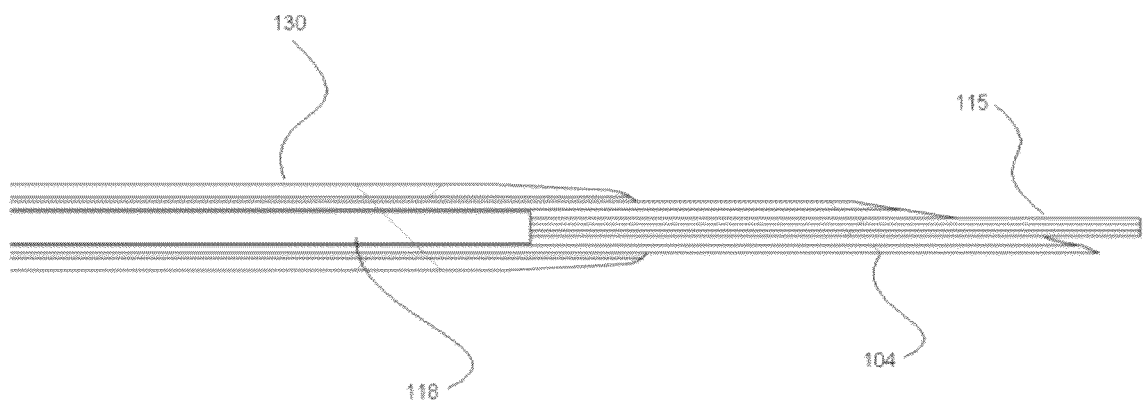

Reference is now made to FIGS. 11A to 11C. After extension of hollow shaft 104 from sleeve 130, the shunt 115 may be deployed from the device 100. The deployment mechanism 103 is a two-stage system. The first stage is engagement of the pusher component 118 and the second stage is retraction of the proximal portion 109 of deployment mechanism 103 to within the distal portion 110 of the deployment mechanism 103. Rotation of the rotating portion 110a of the distal portion 110 of the deployment mechanism 103 sequentially engages the pusher component and then the retraction component.

In the first stage of shunt deployment, the pusher component is engaged and the pusher partially deploys the shunt from the deployment device. During the first stage, rotating portion 110a of the distal portion 110 of the deployment mechanism 103 is rotated, resulting in movement of members 114a and 114b along first portions 113a1 and 113b1 in channels 113a and 113b. Since the first portion 113a1 of channel 113a is straight and runs perpendicular to the length of the rotating portion 110a, rotation of rotating portion 110a does not cause axial movement of member 114a. Without axial movement of member 114a, there is no retraction of the proximal portion 109 to within the distal portion 110 of the deployment mechanism 103. Since the first portion 113b1 of channel 113b runs diagonally along the length of the rotating portion 110a, upwardly toward a proximal end of the deployment mechanism 103, rotation of rotating portion 110a causes axial movement of member 114b toward a proximal end of the device. Axial movement of member 114b toward a proximal end of the device results in forward advancement of the pusher component 118 within the hollow shaft 104. Such movement of pusher component 118 results in partially deployment of the shunt 115 from the shaft 104.

FIGS. 11A to 11C show schematics of the deployment mechanism at the end of the first stage of deployment of the shunt from the deployment device. As is shown FIG. 11A, members 114a and 114b have finished traversing along first portions 113a1 and 113b1 of channels 113a and 113b. Additionally, pusher component 118 has advanced within hollow shaft 104 (FIG. 11B), and shunt 115 has been partially deployed from the hollow shaft 104 (FIG. 11C). As is shown in FIG. 11C, a portion of the shunt 115 extends beyond an end of the shaft 104.

Figure 12:
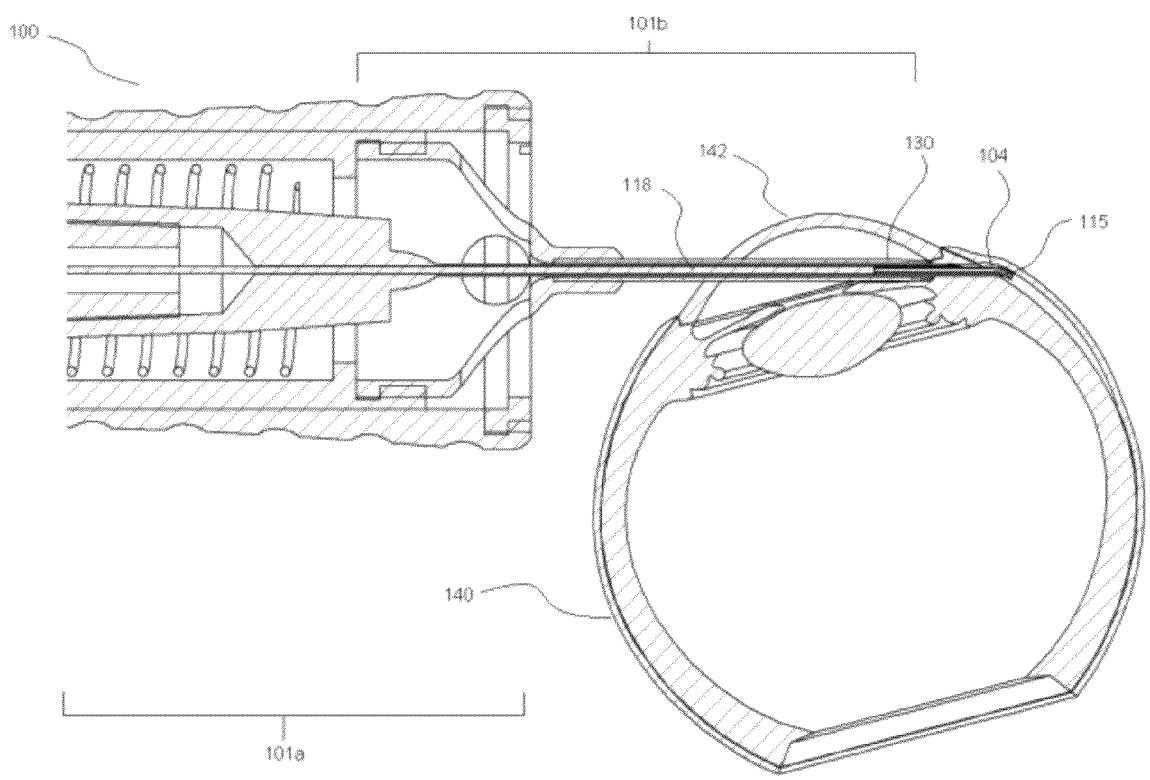
FIG. 12 is a schematic showing the deployment device after completion of the first stage of deployment of the shunt from the device and in to the eye.

FIG. 12 shows device 100 at the end of the first stage of deployment of the shunt 115 from device 100 and into the eye 140. This figure shows that the distal portion 101b of the housing 101 remains retracted within the proximal portion 101a of the housing 101, and that the shaft 104 remains extended from the sleeve 130. As is shown in this figure, pusher 118 has been engaged and has partially deployed shunt 115 from shaft 104. As is shown in this figure, a portion of the shunt 115 extends beyond an end of the shaft 104 and is located in the intra-Tenon's space.

Figure 13A:
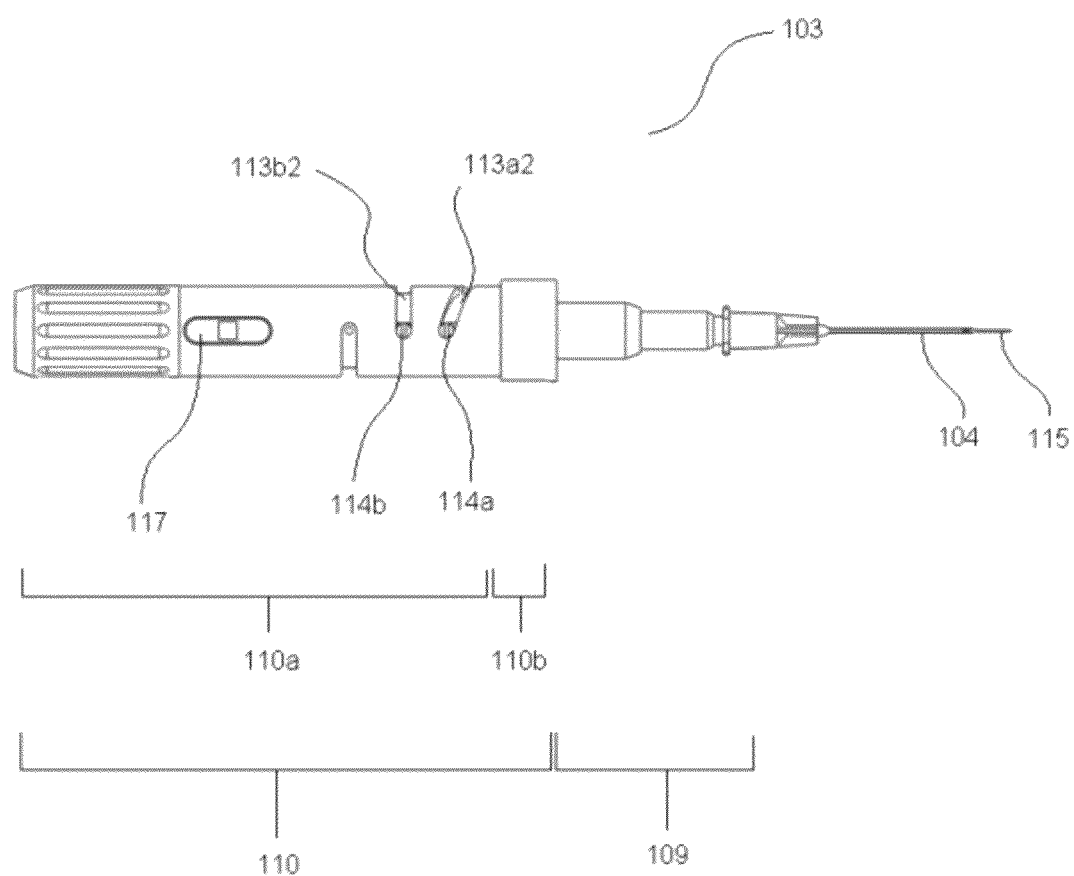
FIG. 13A show a schematic of the deployment mechanism at the end of the second stage of deployment.
Figure 13B:
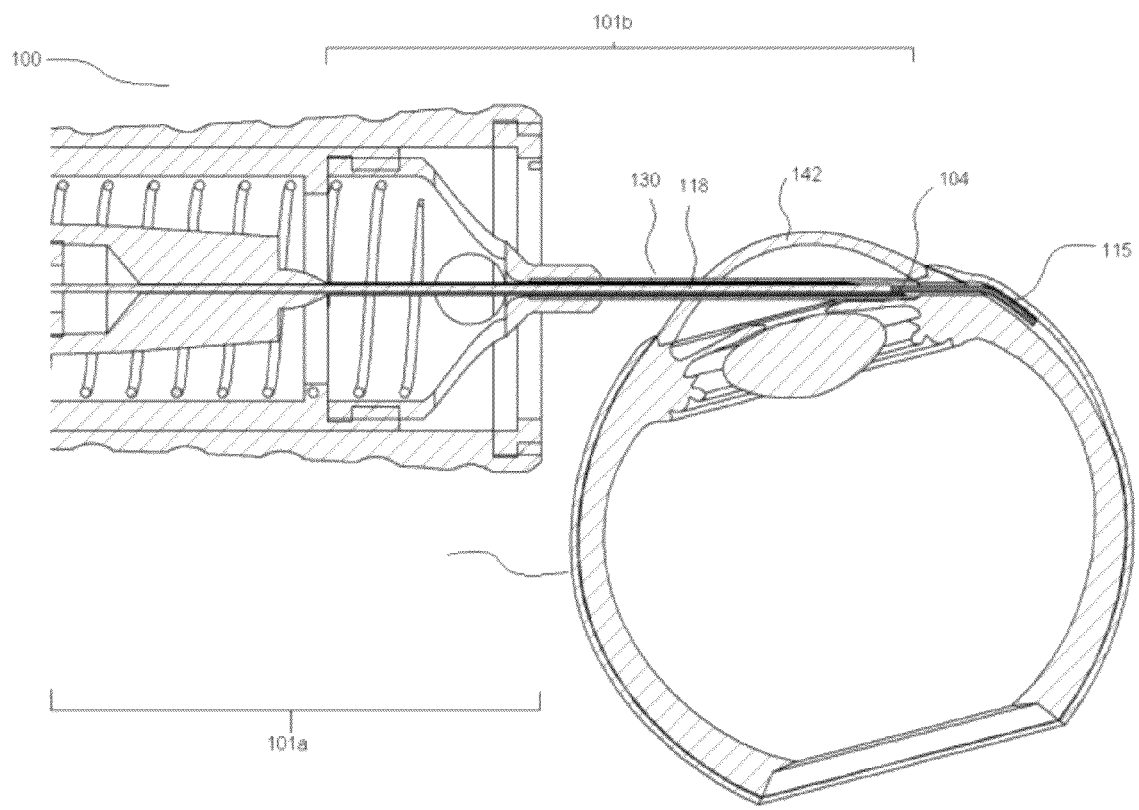
FIG. 13B shows a schematic of the deployment device at the end of the second stage of deployment.
Figure 13C:
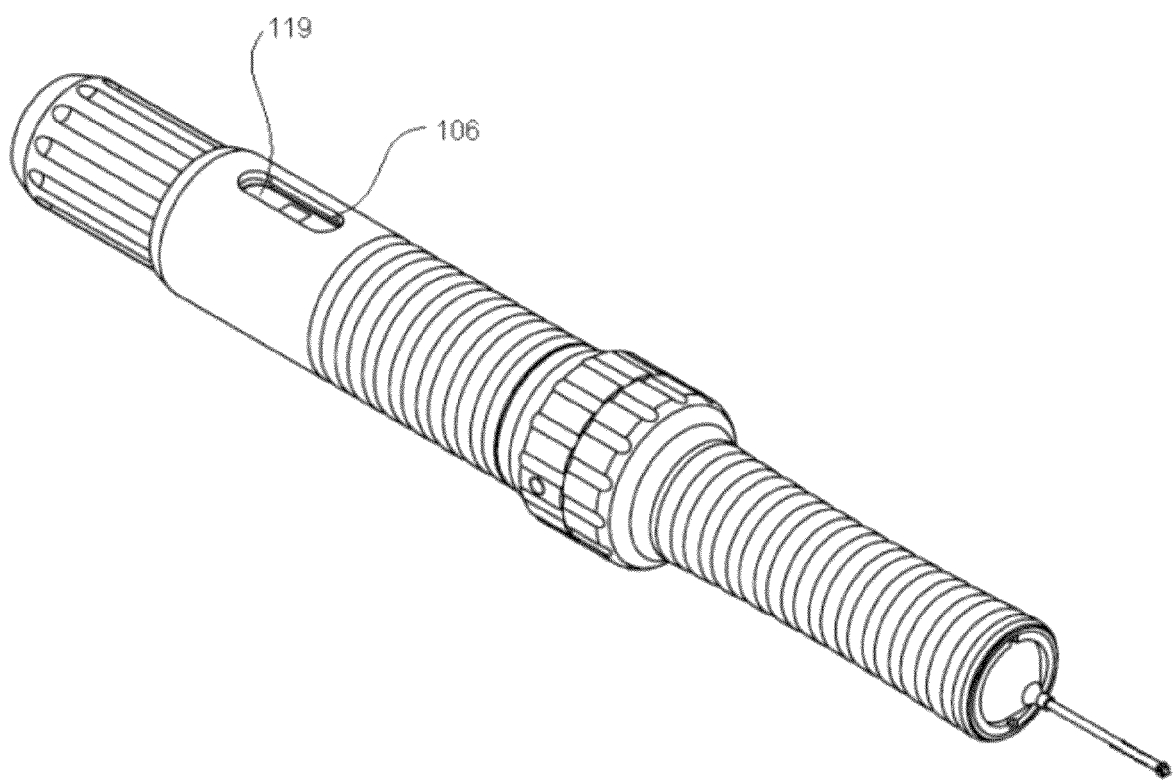
FIG. 13C shows another view of the deployment device at the end of the second stage of deployment.

Reference is now made to FIGS. 13A to 13C. In the second stage of shunt deployment, the retraction component of deployment mechanism is engaged and the proximal portion of the deployment mechanism is retracted to within the distal portion of the deployment mechanism, thereby completing deployment of the shunt from the deployment device. During the second stage, rotating portion 110a of the distal portion 110 of the deployment mechanism 103 is further rotated, resulting in movement of members 114a and 114b along second portions 113a2 and 113b2 in channels 113a and 113b. Since the second portion 113b2 of channel 113b is straight and runs perpendicular to the length of the rotating portion 110a, rotation of rotating portion 110a does not cause axial movement of member 114b. Without axial movement of member 114b, there is no further advancement of pusher 118. Since the second portion 113a2 of channel 113a runs diagonally along the length of the rotating portion 110a, downwardly toward a distal end of the deployment mechanism 103, rotation of rotating portion 110a causes axial movement of member 114a toward a distal end of the device. Axial movement of member 114a toward a distal end of the device results in retraction of the proximal portion 109 to within the distal portion 110 of the deployment mechanism 103. Retraction of the proximal portion 109 results in retraction of the hollow shaft 104. Since the shunt 115 abuts the pusher component 118, the shunt remains stationary at the hollow shaft 104 retracts from around the shunt 115. The shaft 104, retracts completely to within the sleeve 130 of the distal portion 101b of the housing 101. During both stages of the deployment process, the housing 101 remains stationary and in a fixed position.

Referring to FIG. 13A, which shows a schematic of the deployment mechanism at the end of the second stage of deployment of the shunt from the deployment device. As is shown in FIG. 13A, members 114a and 114b have finished traversing along second portions 113a1 and 113b1 of channels 113a and 113b. Additionally, proximal portion 109 has retracted to within distal portion 110, thus resulting in retraction of the hollow shaft 104 to within the housing 101.

FIG. 13B shows a schematic of the device 100 in the eye 130 after the second stage of deployment has been completed. FIG. 13B shows that the distal portion 101b of the housing 101 remains retracted within the proximal portion 101a of the housing 101. As is shown in these FIGS. 13B and 13C, shaft 104 has withdrawn through the sclera 134 and has fully retracted to within sleeve 130. At completion of the second stage of deployment, a distal portion of the shunt 115 has been deployed and resides in the intra-Tenon's space, a middle portion of the shunt 115 spans the sclera, and a proximal portion of shunt 115 has been deployed from shaft 104 yet still resides within sleeve 130. The proximal portion of the shunt 115 still abuts pusher 118.

Referring to FIG. 13C, in the post-deployment configuration, the deployed indicator 119 is visible through slot 106 of the housing 101, providing feedback to the operator that the deployment mechanism 103 has been fully engaged and that the deployment mechanism 103 has completed its second stage of deployment.

Figure 14:
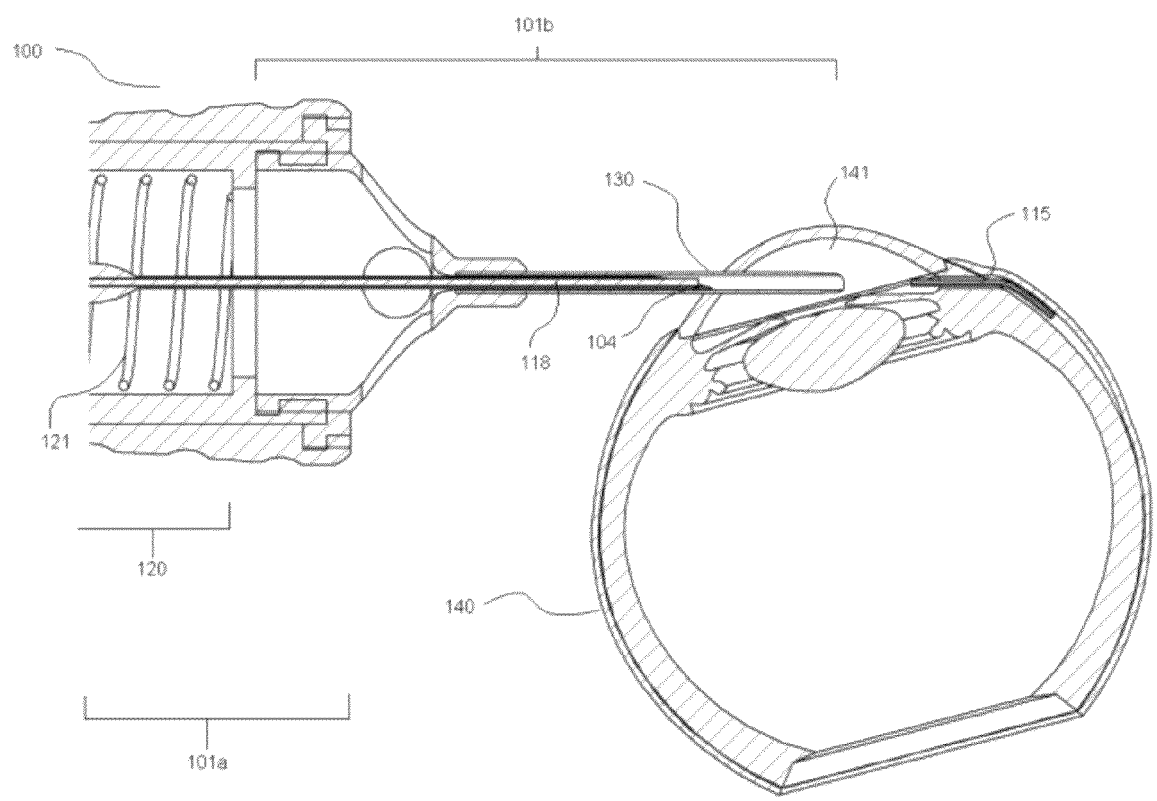
FIG. 14 is a schematic showing the deployment device after completion of deployment of the shunt from the device and in to the eye.

Referring to FIG. 14, which shows a schematic of the device 100 after completion of deployment of the shunt 115 from the device 100 and in to the eye 140. After completion of the second stage of the deployment by the deployment mechanism 103, as indicated to the operator by visualization of deployed indicator 119 through slot 106 of the housing 101, the operator may pull the device 100 from the eye 140. Backward force by the operator reengages spring mechanism 120 and results in uncoiling of spring 121. Uncoiling of spring 121 proceeds as the proximal portion 101a of housing 101 is pulled from the eye 140. Such action causes distal portion 101b to return to its extended state within proximal portion 101a of housing 101. Continued backward force by the operator continues to pull the device 100 from the eye 140. As the device 100 is continued to be pulled from the eye, the sleeve 130 is also pulled backward and the proximal portion of the shunt 115 is exposed from within the sleeve 130 and resides within the anterior chamber 141 of the eye 140. The operator continues to apply backward force until the device 100 is completely withdrawn from the eye 140.

COMBINATIONS OF EMBODIMENTS

As will be appreciated by one skilled in the art, individual features of the invention may be used separately or in any combination. Particularly, it is contemplated that one or more features of the individually described above embodiments may be combined into a single shunt.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method for treating closed angle glaucoma, the method comprising:
   inserting into an eye a deployment device configured to hold an intraocular shunt, the device comprising a sleeve with a protrusion at a distal end of the sleeve, the protrusion (a) having a generally linear and generally rounded distalmost edge extending in a direction transverse to the longitudinal axis of the sleeve, and (b) protruding radially outwardly, relative to a longitudinal axis of the sleeve, from a portion of the sleeve proximal to the protrusion;
   using the device to re-open an at least partially closed anterior chamber angle of an eye by moving the protrusion toward the anterior chamber angle; and
   advancing the shunt from the device into eye tissue while the protrusion is in contact with tissue at the anterior chamber angle.

2. The method according to claim 1, wherein advancing the shunt comprises forming a flow path from an anterior chamber of the eye to an area of lower pressure.

3. The method according to claim 2, wherein the area of lower pressure is selected from the group consisting of: intra-Tenon's space, the subconjunctival space, the episcleral vein, the suprachoroidal space, and Schlemm's canal.

4. The method according to claim 1, wherein the inserting step comprises inserting the device through the cornea.

5. The method according to claim 1, further comprising determining, without use of an optical apparatus that contacts the eye, that a distal portion of the device is at a position at the anterior chamber angle of the eye.

6. The method according to claim 5, wherein the optical apparatus is a goniolens.

7. A method for treating closed angle glaucoma, the method comprising:
inserting into an eye a deployment device (i) holding an intraocular shunt and (ii) comprising a sleeve, the sleeve comprising a wedge-shaped protrusion having a generally rounded edge extending transversely to a longitudinal axis of the sleeve at a distal end of the sleeve;
re-opening an at least partially closed anterior chamber angle of an eye, the re-opening comprising advancing the protrusion toward an at least partially closed anterior chamber angle of the eye until the protrusion contacts tissue and then continuing advancement of the protrusion into the anterior chamber angle without entering tissue of the eye; and
after advancing the protrusion fully into the anterior chamber angle, advancing the shunt relative to the sleeve into tissue of the eye.

8. The method according to claim 7, wherein the device further comprises a hollow shaft that is movable within the sleeve, and the method further comprising distally advancing the hollow shaft relative to the sleeve after advancement of the distal portion into the anterior chamber angle without entering tissue of the eye.

9. The method according to claim 7, wherein the protrusion is formed integrally with the distal end of the sleeve.

10. The method according to claim 7, wherein the protrusion surrounds the distal end of the sleeve.

11. The method according to claim 7, wherein the protrusion extends around only a portion of the sleeve.

12. The method according to claim 7, wherein the protrusion comprises a collar that surrounds the distal end of the sleeve.

13. The method according to claim 7, wherein the protrusion comprises a substantially flat bottom portion and a top portion that is oriented at an acute angle with respect to the bottom portion.

14. The method according to claim 7, wherein the inserting step comprises inserting the device through the cornea.

15. The method according to claim 7, further comprising determining, without use of an optical apparatus that contacts the eye, that a distal portion of the device is at a position at the anterior chamber angle of the eye.

16. The method according to claim 15, wherein the optical apparatus is a goniolens.

17. A method for treating closed angle glaucoma, the method comprising:
inserting into an eye a deployment device (i) holding an intraocular shunt and (ii) comprising a sleeve, the sleeve having a lumen and a distal portion comprising a distal end of the sleeve, the lumen having a longitudinal axis, the distal portion comprising a wedge-shaped protrusion having a larger external dimension in a direction transverse to the longitudinal axis than has a portion of the sleeve proximal to the distal portion;
re-opening an at least partially closed anterior chamber angle of an eye by advancing the distal portion into an at least partially closed anterior chamber angle of the eye; and
with the protrusion fitted within the anterior chamber angle, advancing the shunt relative to the sleeve into tissue of the eye.

18. The method according to claim 17, wherein advancing the shunt comprises forming a flow path from an anterior chamber of the eye to an area of lower pressure.

19. The method according to claim 18, wherein the area of lower pressure is selected from the group consisting of: intra-Tenon's space, the subconjunctival space, the episcleral vein, the suprachoroidal space, and Schlemm's canal.

20. The method according to claim 17, wherein the inserting step comprises inserting the device through the cornea.

21. The method according to claim 17, further comprising determining, without use of an optical apparatus that contacts the eye, that a distal portion of the device is at a position at the anterior chamber angle of the eye.

22. The method according to claim 21, wherein the optical apparatus is a goniolens.

23. The method according to claim 17, wherein the device further comprises a hollow shaft that is movable within the sleeve, and the method further comprising distally advancing the hollow shaft relative to the sleeve after advancing the distal portion into the anterior chamber angle.

24. The method according to claim 17, wherein the distal portion comprises a distally facing convex surface.

* * * * *